(12) United States Patent
Kumar et al.

(10) Patent No.: US 6,312,260 B1
(45) Date of Patent: Nov. 6, 2001

(54) ONE-STEP THREADED IMPLANT

(75) Inventors: Ajay Kumar, Palmdale; Don Kennard, Huntington Beach, both of CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/374,087

(22) Filed: Aug. 12, 1999

Related U.S. Application Data

(60) Provisional application No. 60/096,332, filed on Aug. 12, 1998.

(51) Int. Cl.[7] ............................................. A61C 8/00
(52) U.S. Cl. ................................... 433/174; 206/368
(58) Field of Search ................................. 433/174, 173, 433/201.1, 176; 206/431, 368

(56) References Cited

U.S. PATENT DOCUMENTS

| | | |
|---|---|---|
| 2,347,567 | 4/1944 | Kresse . |
| 3,346,135 | 10/1967 | Haitsch . |
| 4,158,256 | 6/1979 | Wiland et al. . |
| 4,187,609 | 2/1980 | Edelman . |
| 4,465,463 | 8/1984 | Olde . |
| 4,553,942 | 11/1985 | Sutter . |
| 4,600,388 | 7/1986 | Linkow . |
| 4,856,648 | 8/1989 | Krueger . |
| 4,856,994 | 8/1989 | Lazzara et al. . |
| 4,955,811 | 9/1990 | Lazzara et al. . |
| 5,013,242 | 5/1991 | Prezmecky . |
| 5,030,096 | 7/1991 | Hurson et al. . |
| 5,062,800 | 11/1991 | Niznick . |
| 5,100,323 | 3/1992 | Friedman et al. . |
| 5,105,690 | 4/1992 | Lazzara et al. . |
| 5,158,458 | 10/1992 | Perry . |
| 5,213,500 | 5/1993 | Salazar et al. . |
| 5,254,005 | 10/1993 | Zuest . |
| 5,302,125 | 4/1994 | Xownacki et al. . |
| 5,306,309 | 4/1994 | Wagner et al. . |
| 5,312,254 | 5/1994 | Rosenlicht . |
| 5,322,443 | 6/1994 | Beaty . |
| 5,336,090 | * 8/1994 | Wilson, Jr. et al. .................. 433/173 |
| 5,338,196 | * 8/1994 | Beaty et al. .......................... 433/173 |
| 5,368,160 | * 11/1994 | Leuschen et al. .................... 433/174 |
| 5,368,483 | 11/1994 | Sutter et al. . |
| 5,417,570 | 5/1995 | Zuest et al. . |
| 5,437,550 | 8/1995 | Beaty et al. . |
| 5,462,436 | 10/1995 | Beaty . |
| 5,538,428 | 7/1996 | Staubli . |
| 5,558,230 | 9/1996 | Fischer et al. . |
| 5,564,924 | 10/1996 | Kwan . |
| 5,569,037 | * 10/1996 | Moy et al. ........................... 433/173 |

(List continued on next page.)

FOREIGN PATENT DOCUMENTS

| | | |
|---|---|---|
| 2232009 | 3/1998 | (CA) . |
| 0 630 621 A2 | 12/1994 | (EP) . |
| WO 97/20518 | 6/1997 | (WO) . |
| WO 98/53755 | 5/1998 | (WO) . |

*Primary Examiner*—Todd E. Manahan
(74) *Attorney, Agent, or Firm*—Knobbe, Martens, Olson & Bear, LLP

(57) ABSTRACT

A threaded dental implant assembly is provided for insertion into a pre-drilled bore in the jawbone is disclosed. The threaded dental implant assembly includes a threaded implant body to which is attached a healing cap for covering the central socket in the implant body during the healing period. The healing cap is mechanically coupled to the implant body before the insertion procedure by a coupling screw extending through bore in the healing cap into the central socket of the implant body. A recess in the bottom of the healing cap mates with a protrusion on the top of the implant body such that the healing cap is prevented from rotating relative to the implant body. A tool engages the top of the healing cap for easy manipulation of the implant body/healing cap during the insertion procedure. The tool is disengaged from the healing cap after the insertion procedure thereby leaving the implant body and healing cap in the jawbone.

46 Claims, 21 Drawing Sheets

U.S. PATENT DOCUMENTS

| | | |
|---|---|---|
| 5,582,299 | 12/1996 | Lazzara et al. . |
| 5,622,500 | 4/1997 | Niznick . |
| 5,636,991 | 6/1997 | Mays . |
| 5,651,675 | 7/1997 | Singer . |
| 5,683,464 | 11/1997 | Wagner et al. . |
| 5,692,904 | 12/1997 | Beaty et al. . |
| 5,733,124 | 3/1998 | Kwan . |
| 5,755,575 | 5/1998 | Biggs . |
| 5,904,483 | 5/1999 | Wade . |
| 5,961,330 | 10/1999 | Hanson . |
| 5,964,591 | 10/1999 | Beaty et al. . |
| 5,967,305 | 10/1999 | Blonder et al. . |
| 5,979,643 | 11/1999 | Blonder et al. . |

\* cited by examiner

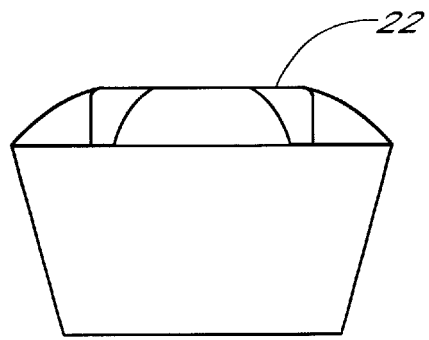
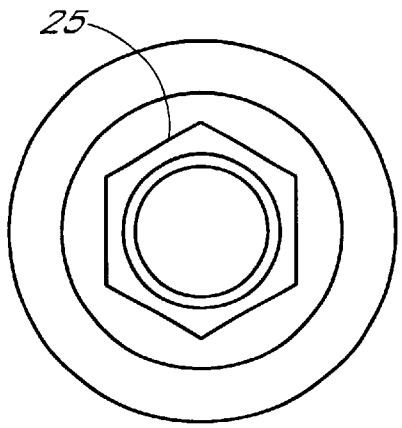
FIG. 4A          FIG. 4B
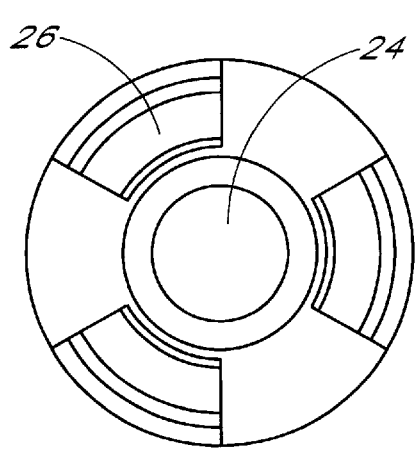
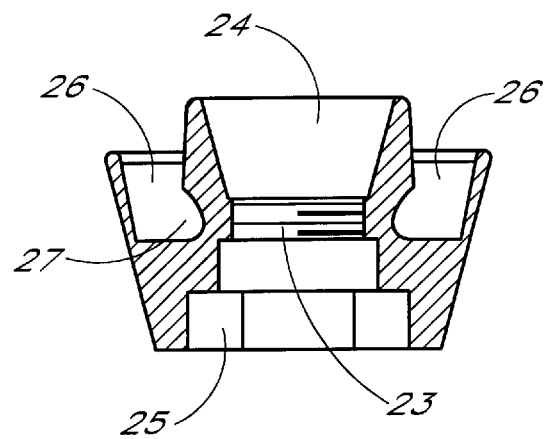
FIG. 4C          FIG. 4D

ONE-STEP THREADED IMPLANT

RELATED APPLICATIONS

This application claims the benefit of U.S. Provisional Application No. 60/096,332, filed Aug. 12, 1998.

BACKGROUND OF THE INVENTION

1. Field of the Invention

The present invention relates generally to dental implants and, more particularly, to a threaded implant body with a pre-attached healing cap that can be quickly and safely placed into the jaw as a single unit.

2. Background of the Related Art

Dental implants are placed in the jaw to provide support for a dental restoration, fixed bridge or removable partial denture. Dental implants provide good chewing function and also improve the patient's cosmetic appearance thereby allowing the patient to smile, speak, and interact with others with greater confidence.

One type of dental implant widely used in the industry is typically referred to as a "threaded" implant. Threaded implants have an externally threaded body portion which is screwed into a pre-drilled hole (i.e. an osteotomy) in the patient's upper or lower jawbone. Typically, the threaded implant body is formed with a central threaded socket accessible through the overlying gum tissue for receiving and supporting one or more dental attachments or components. Types of attachments and components that are received by the central socket include healing caps, impression copings and abutments. In turn, some of these attachments and components are useful to fabricate and/or support the prosthodontic restoration.

Dental implants are typically packaged as an assembly including all the tools necessary for the insertion of the implant into an osteotomy formed in the jaw. A typical threaded implant assembly includes a threaded implant body, an implant carrier, an insertion post, a coupling screw and a healing cap. The implant carrier, insertion post, and coupling screw are tools which are used during the insertion of the implant body. Typically, the implant carrier, insertion post and coupling screw are discarded after the implant body has been inserted into the osteotomy. The healing cap seals and protects the central socket of the implant body during the initial healing period.

During the insertion of a conventional threaded implant, the insertion post is mechanically coupled to the top of the implant body by a coupling screw which traverses a central through-cavity in the insertion post and is threaded into the central threaded socket in the implant body. Typically, the bottom end of the insertion post is formed with a hexagonal cavity that irrationally mates with a corresponding hexagonal protrusion formed on the top of the implant body thereby preventing any relative rotation between the insertion post and implant body while coupled.

An implant carrier is releasably coupled to the top of the insertion post and provides the dental practitioner with a means to grip and manipulate the assembly during the initial implantation procedure. Typically, the implant carrier is formed with a generally hexagonal internal passage at its bottom end which mates with a generally hexagonal outer surface near the top of the insertion post. The dental practitioner uses the implant carrier to manipulate the implant body into the proper location within the jawbone. Torque is applied to the implant carrier which is transferred, via the insertion post, to the threaded implant body.

In use, the first step of a typical implantation procedure involves making an incision in the patient's gum tissue. A portion of the gum tissue is then folded back and an osteotomy is drilled in the jawbone. The diameter of the osteotomy is equal to or slightly smaller than the diameter of the implant body. The implant carrier is then used to transport the threaded implant assembly to the surgical site. The implant carrier is gripped by the practitioner and is used to manipulate the implant body into the correct position and then to partially screw the threaded implant body into the osteotomy.

Once the implant body has been initially placed in the osteotomy and tightened manually, the implant carrier is decoupled from the insertion post and is removed from the surgical site. If necessary, a suitable wrench or dental hand piece is then used to engage the insertion post and drive the implant to its final depth within the osteotomy. The coupling screw is then removed and the insertion post is decoupled from the implant body leaving only the implant body in the patient's mouth.

The healing cap is housed in a cavity formed in the top of the implant carrier where it is contained by a paper barrier until needed. At this point, the healing cap is removed from the implant carrier and is threaded into the central socket of the implant body. Typically, a tool with a hexagonal tip is inserted into a corresponding mating hexagonal recess located in the top center of the healing cap and is used to apply torque to tighten the healing cap. The healing cap protects the implant socket against bone or tissue in growth during the initial healing period, and also prevents the entry of bacteria or other contaminants into the central socket of the implant body.

The insertion of the implant body and healing cap is then followed by an initial healing period in which the bone is allowed to surround and retain the implant (i.e. "osseointegrate" with the implant) and the gum tissue is allowed to heal over the implant body and healing cap. For implants placed in the mandible, healing typically requires about three months; for implants in the maxilla, the healing period typically requires about six months.

After the implant body has sufficiently osseointegrated with the jawbone, the gum tissue is re-opened by making an incision and the gum tissue is folded back to expose the healing cap. The hexagonal tool is inserted into the recess in the top of the healing cap and torque is applied to rotate the healing cap out of the implant socket and to remove it from the implant body. During this step of the procedure, great care must be used to remove the healing cap without disturbing the position of the implant body. Any disturbance of the implant body during the removal of the healing cap could damage the osseointegration between the implant body and the jawbone. Damage to the osseointegration is very undesirable and could endanger the entire restoration process by destabilizing the implant. In addition, any movement of the implant body could result in gaps or spaces between the implant body and jawbone which could in turn lead to infection by bacteria and/or other contaminants After the healing cap has been unscrewed and removed from the patient's mouth, a suitable healing abutment is inserted into the central socket. The healing abutment extends through the gum tissue overlying the implant site. A second healing period then ensues in which the gum tissue is allowed to heal around the post-osseointegration healing abutment. Typically, this second healing period lasts from four to eight weeks.

After the second healing period has ended, the healing abutment is removed from the implant body. Typically, an impression is taken of the patient's mouth to fabricate a prosthesis or dental restoration. An abutment supporting the final restoration is then attached to the implant body. Lastly, the restoration is cemented or screwed to the abutment and/or implant body to complete the placement of the prosthodontic restoration in the patient's mouth.

The conventional threaded dental implant described above is commonly used by dental practitioners and is preferred for its ability to achieve a good mechanical connection between the implant body and the jawbone. However, this type of threaded implant suffers from several significant shortcomings. In particular, the insertion of a conventional threaded dental implant is a difficult and time consuming procedure. The procedure is difficult because, after the implant body has been inserted in the osteotomy, the coupling screw holding the insertion post to the implant body must be removed very carefully such that the position of the implant body is not affected. Any movement of the implant body is undesirable because precise placement of the implant body is critical to the success of the implant procedure. Similarly, the attachment of the healing cap must also be performed with great care. If the healing cap is not tightened sufficiently, the patient runs the risk of infection in the gap between the implant body and the healing cap or in the implant socket. On the other hand, if too much torque is applied, it may be difficult or impossible to remove the healing cap after the healing period without affecting the position of the implant body or damaging the osseointegration between the implant body and the jawbone.

The procedure for inserting a conventional threaded dental implant is time consuming because of the numerous steps involved in the procedure. After inserting the implant body, the dental practitioner must first remove both the insertion post and coupling screw from the implant body and then insert and tighten the healing cap to cover the exposed socket. Each of these steps can be very cumbersome and allows for the possibility of human error. Additionally, there is the possibility that the insertion post, coupling screw and the healing cap, which are generally small in size, may inadvertently be lost in the patient's mouth during the implantation procedure.

The above shortcomings were addressed in a threaded dental implant design disclosed in U.S. Pat. No. 5,755,575 to Biggs. In Biggs, the healing cap is attached to the implant body before the implant body is inserted into the patient's mouth to reduce the overall number of steps required in the dental restoration procedure. In Biggs, the healing cap is also used as a driver to screw the implant body into the osteotomy. Although Biggs reduces the number of steps involved in the implantation procedure, Biggs suffers from a further shortcoming because the healing cap has no threads and is press-fitted into the implant socket. As a result, there is no tension force pulling the healing cap down against the top of the implant body. Without any tension, there is no assurance that the healing cap will be touching the implant body and a gap may result between the healing cap and implant body. Any gap between the healing cap and the implant body is disadvantageous because it could lead to infection by bacteria or other contaminants. Therefore, Biggs does not provide sufficient protection against infection.

Another type of dental implant widely used in the industry is typically referred to as a "cylindrical" implant. Cylindrical implants have also been designed wherein the healing cap is pre-attached to the implant body to simplify the implantation procedure. However, cylindrical implants are not suitable in all situations and do not provide desired initial stability within the jawbone as provided by a threaded implant.

Thus, there exists a need for an improved threaded dental implant in which the healing cap is pre-attached to the implant body such that both the implant body and healing cap can be inserted simultaneously into the patient's mouth in a simple one-step procedure. It is also desirable that such a pre-attached healing cap be pulled down against the implant body thereby sealing off the implant socket and minimizing the risk of infection during the healing period.

SUMMARY OF THE INVENTION

It is, accordingly, an object of this invention to provide an apparatus for placing a threaded dental implant and healing cap into an osteotomy in a more efficient and safe manner than has heretofore been available with conventional threaded implants.

Additional objectives and advantages of the invention will be set forth in part in the description which follows, and in part will be apparent from the description, or may be learned by practice of the invention. The objectives and advantages of the invention may be realized and attained by means of the instrumentalities and combinations particularly pointed out in the appended claims.

To achieve the foregoing objectives, and in accordance with the purpose of the invention, as embodied and broadly described herein, there is provided a one-step threaded implant generally comprising a threaded implant body for insertion into an osteotomy, a pre-attached healing cap for covering the central socket of the implant body, a coupling screw for coupling the healing cap to the implant body, and an adapter/implant carrier which releasably engages the top of the healing cap and provides a means for the practitioner to manipulate the implant body into the osteotomy.

The present invention overcomes some or all of the disadvantages of conventional threaded implant assemblies by providing a one-step threaded dental implant in which the implant body and a pre-attached healing cap can be inserted simultaneously in a simple one-step procedure. The present invention significantly decreases the difficulty of the implantation procedure and saves time by reducing the number of steps required in the procedure. The present invention also provides for a tight seal between the healing cap and the implant body, thereby protecting the implant socket from bone or tissue in growth or infection. In addition, because there is no insertion post to decouple after the implant body is inserted into the jaw, the present invention also eliminates the possibility of losing small components in the patient's mouth. Also, since the healing cap is pre-attached to the implant, the chances of it being over-tightened are eliminated.

In accordance with one embodiment the invention provides a one-step threaded implant that can be delivered to the surgical site with the healing cap already attached to the implant body. The healing cap is mechanically coupled to the implant body by a coupling screw which passes through a bore in the center of the healing cap and is threadably engaged in the socket of the implant body. The coupling screw is pre-installed by the manufacturer of the implant assembly and therefore may be precision tightened to the proper torque setting. The top of the healing cap is advantageously formed with one or more recesses for receiving a torque wrench or other suitable tool for driving the implant assembly into the osteotomy. The bottom of the healing cap is advantageously formed with a hexagonal recess or other suitably shaped recess or protrusion that mates with a corresponding recess or protrusion on the top of the implant body. This allows torque transmission to take place from the torque wrench to the healing cap, and from the healing cap directly to the implant, thereby preventing over-tightening of the coupling screw. It also prevents relative rotation between the healing cap and the implant body.

In another embodiment the present invention provides an adapter that releasably engages the healing cap during the insertion process. The adapter has prongs that are inserted into corresponding slots formed in the top of the healing cap. After the implant body is inserted, the adapter is disengaged from the healing cap by pulling gently on the adapter or rocking the adapter to disengage the prongs from the slots. The adapter may be integrated with an implant carrier or an implant carrier may be included as a separate component attached thereto. In both embodiments, the implant carrier is formed with a flange that provides a means for manipulating the implant body and for applying torque to at least initially thread the implant body into an osteotomy.

In another embodiment, the present invention provides a threaded dental implant assembly for insertion into a pre-drilled bore in the jawbone. The threaded dental implant assembly includes a threaded implant body to which is attached a healing cap for covering the central socket in the implant body during the healing period. The healing cap is mechanically coupled to the implant body before the insertion procedure by a coupling screw extending through bore in the healing cap into the central socket of the implant body. A recess in the bottom of the healing cap mates with a protrusion on the top of the implant body such that the healing cap is prevented from rotating relative to the implant body. A tool engages the top of the healing cap for easy manipulation of the implant body/healing cap during the insertion procedure. The tool is disengaged from the healing cap after the insertion procedure thereby leaving the implant body and healing cap in the jawbone.

In another embodiment the present invention provides a threaded dental implant assembly implantable within an osteotomy formed in a jawbone. The dental implant assembly generally comprises a cylindrical implant body having a top end and a bottom end. The implant body has external threads for engagement with the osteotomy formed in the jawbone. The bottom end of the implant body is insertable into the osteotomy such that the implant body may be threaded into the osteotomy. The implant body further has a threaded central socket extending from the top end toward the bottom end. The socket is open at the top end of the implant body to facilitate receiving of a coupling screw. The implant body has a protrusion attached to and extending away from the top end. A healing cap is provided and is securely coupled to the implant body before the implant body is inserted into the osteotomy. The healing cap has a top, a bottom and a central bore extending therethough. The healing cap further has a recess which mates with the protrusion in the implant body to prevent relative rotation of the healing cap when the healing cap is coupled to the implant body. A coupling screw is provided and securely couples the healing cap to the implant body. An adapter is provided and is engaged to the top of the healing cap during the implantation procedure. The adapter allows torque to be applied through the healing cap to the implant body to thread the implant body into the osteotomy.

In another embodiment the present invention provides a threaded dental implant assembly comprising an implant body and a healing cap secured thereto by a coupling screw. The implant body has a top end and a bottom end and a central socket extending through the top end. The implant body further has a protrusion extending from the top end for engaging a corresponding recess formed in the healing cap. The healing cap has a central bore and a recess for mating with the protrusion in the top end of the implant body. A coupling screw is provided and extends through the central bore of the healing cap and into the central socket in the implant body and securely attaches the healing cap to the implant body prior to insertion in the osteotomy.

In another embodiment the present invention provides a two-part healing cap assembly for protecting a socket in an implant body during an initial healing period. The healing cap assembly generally comprises a cap portion having a central bore and a coupling screw insertable through the central bore for securing the cap portion to the implant body. The cap portion further includes a recess for mating with a corresponding protrusion formed in the implant body.

In another embodiment the present invention provides a method for inserting a dental implant into an osteotomy. In accordance with the method, a hole is drilled in the jawbone beneath the gum tissue. A threaded implant having a pre-attached healing cap is then transported to the hole in the jawbone and inserted therein. Torque is applied to the implant body via a tool engaging the top of the healing cap to thread the implant body into the osteotomy. Once the implant is properly seated in the osteotomy, the tool is disengaged from the healing cap.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which:

FIG. 4A is a side view of the healing cap shown in FIG. 2;

FIG. 4B is a bottom view of the healing cap shown in FIG. 4A;

FIG. 4C is a top view of the healing cap shown in FIG. 4A;

FIG. 4D is a cross-sectional view of the healing cap shown in FIG. 4A;

DETAILED DESCRIPTION OF THE PREFERRED EMBODIMENTS

Figure 1:
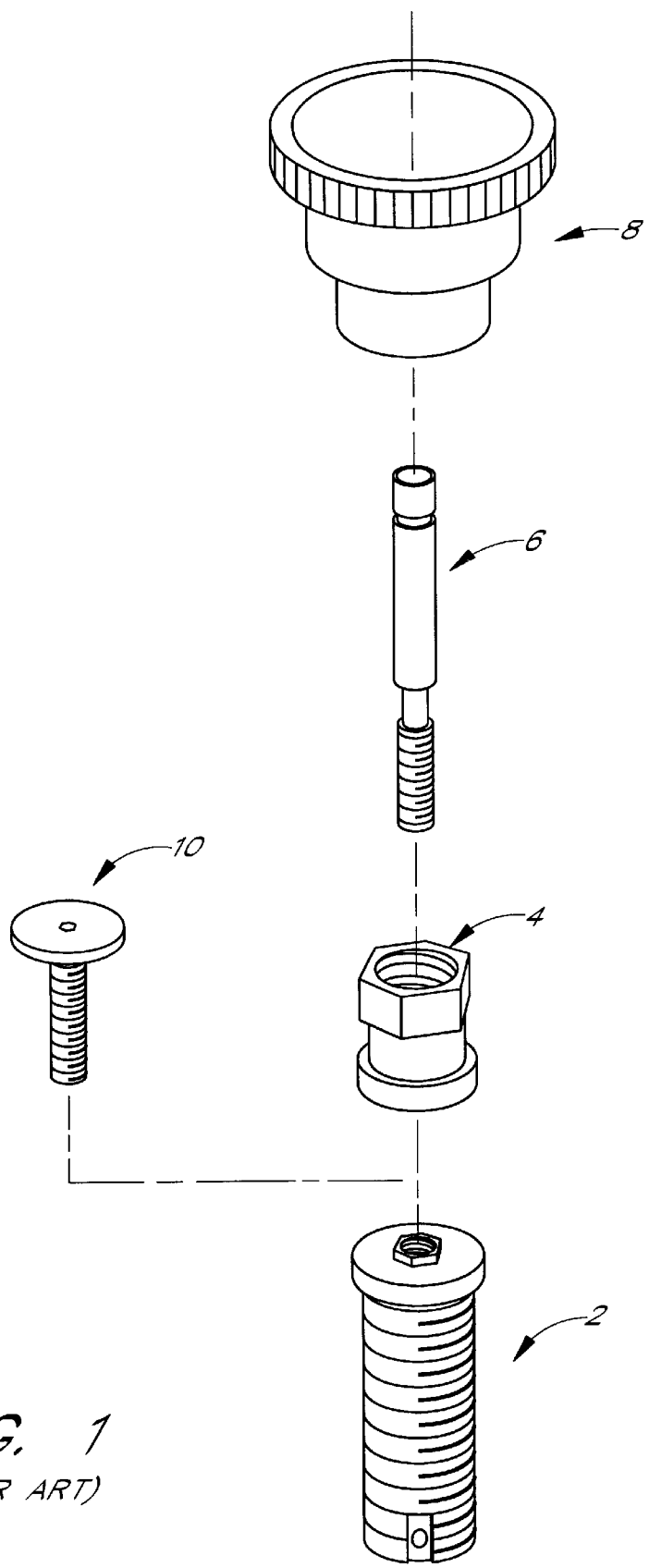
FIG. 1 is an exploded view of a conventional threaded dental implant assembly in accordance with the prior art.

The insertion of a conventional threaded implant body into an osteotomy formed in a jawbone is a difficult and time consuming procedure. As shown in FIG. 1, a conventional implant assembly typically includes an implant body 2, an insertion post 4 coupled to the implant body 2 by a coupling screw 6, an implant carrier 8 coupled to the insertion post 4, and a healing cap 10. After drilling a hole (i.e. an osteotomy) in the patient's jawbone, the dental practitioner grips the implant carrier 8, transports the implant assembly to the surgical site, and manipulates the implant body 2 into position over the osteotomy. Once the implant body 2 is properly positioned, the dental practitioner applies torque to the implant carrier 8 to begin screwing the implant body into the osteotomy. If necessary, the implant carrier 8 is then decoupled from the insertion post 4 and a tool is attached to the insertion post to drive the implant body the rest of the way into the osteotomy. After the implant body is properly seated, the insertion post is decoupled from the implant body by removing the coupling screw. To protect against infection, a healing cap 10 is screwed into the central socket of the implant body to cover the socket during the initial healing period.

The process of screwing the healing cap into the socket of the implant body can itself be very difficult and requires much attention to detail. If the healing cap is tightened too much, the healing cap may be difficult or impossible to remove after the healing period without disturbing the position of the implant body and/or damaging the osseointegration between the implant body and the jawbone. On the other hand, if the healing cap is not tightened sufficiently, infection by bacteria or other contaminants may result in the implant body socket or in the gap between the healing cap and the implant body. In addition, the socket in the implant body may fill with blood or other bodily fluids prior to attaching the healing cap if adequate care is not taken.

Figure 2:
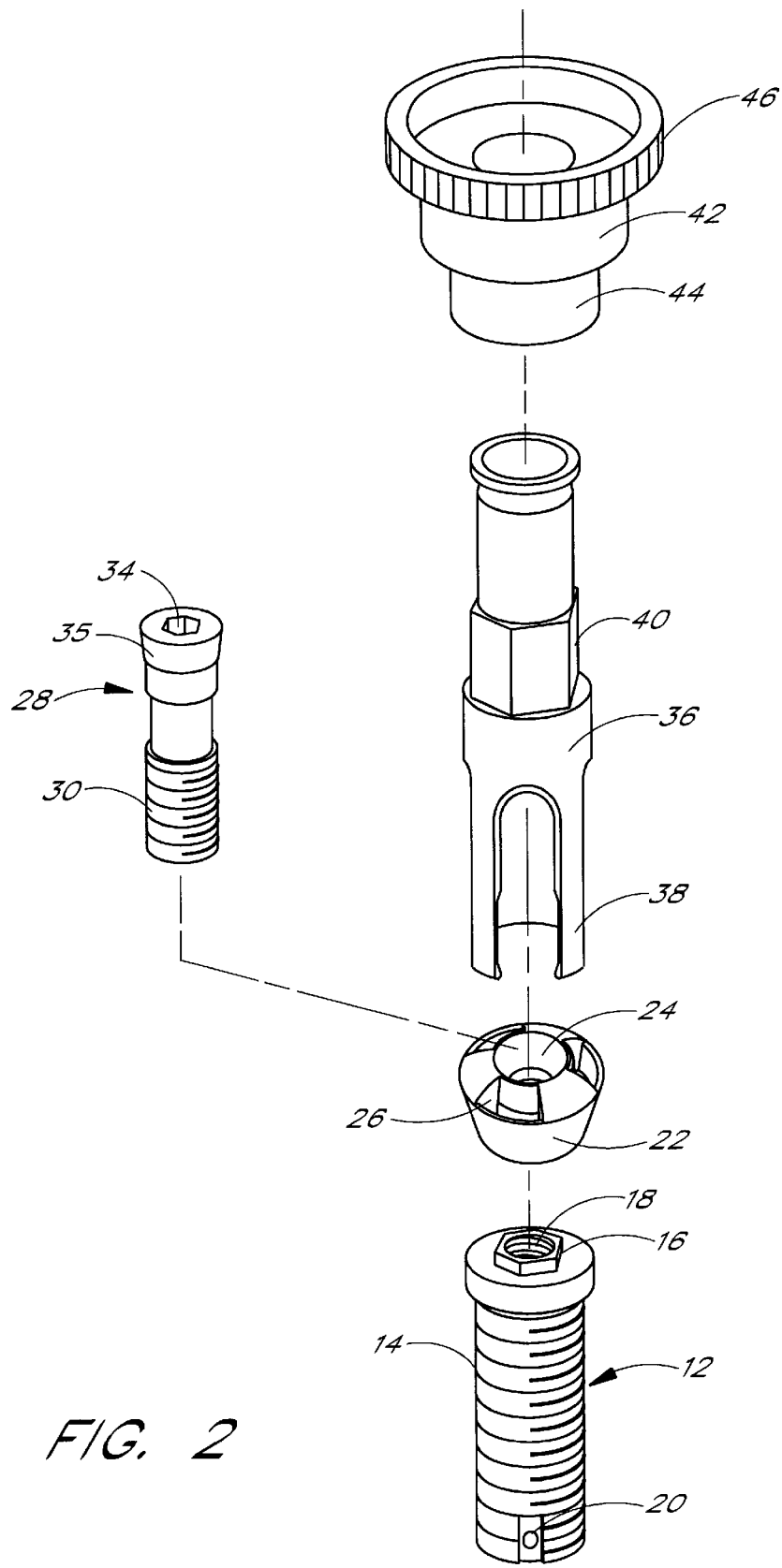
FIG. 2 is an exploded view of one embodiment of a one-step threaded dental implant assembly having features and advantages of the present invention.
Figure 3A:
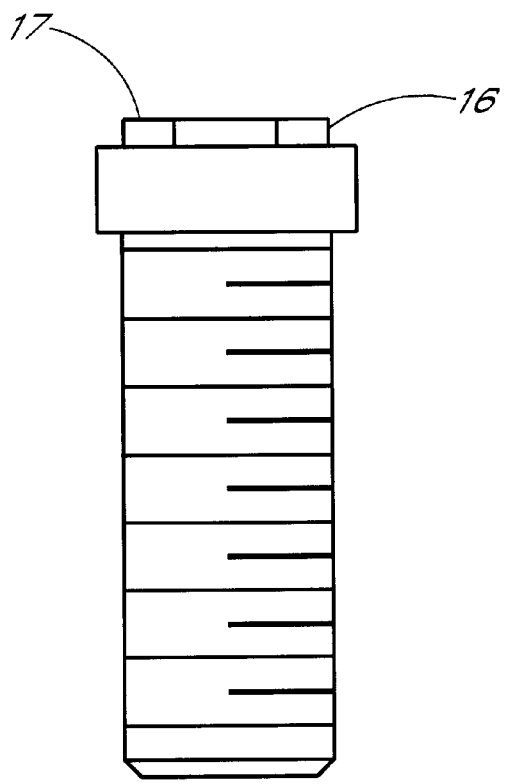
FIG. 3A is a side view of the implant body shown in FIG. 2.
Figure 3B:
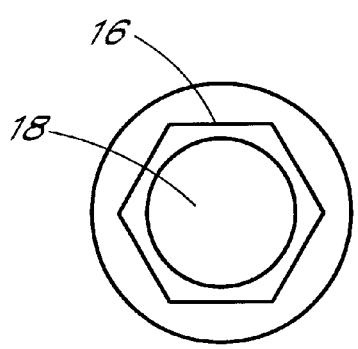
FIG. 3B is a top view of the implant body shown in FIG. 3A.

Reference will now be made in detail to preferred embodiments of the invention, which are illustrated in the accompanying drawings. FIG. 2 shows one preferred embodiment of a one-step threaded implant assembly having features and advantages in accordance with this invention. Implant body 12 is generally cylindrical in shape and has external threads 14 for engagement with the jawbone. As shown in FIGS. 3A and 3B, implant body 12 includes a threaded socket 18 which is open at the top of implant body 12 and extends longitudinally partway into the implant body. Hexagonal projection 16 is formed at the top of implant body 12 and is concentrically arranged around threaded socket 18. Hexagonal projection 16 is integrally attached to and extends away from implant body 12. The top surface 17 of hexagonal projection 16 is generally planar and is parallel to the top surface of implant body 12. The bottom end of implant body 12 includes a thread-forming portion 20 for allowing self-tapping of the threaded implant.

Figure 4E:
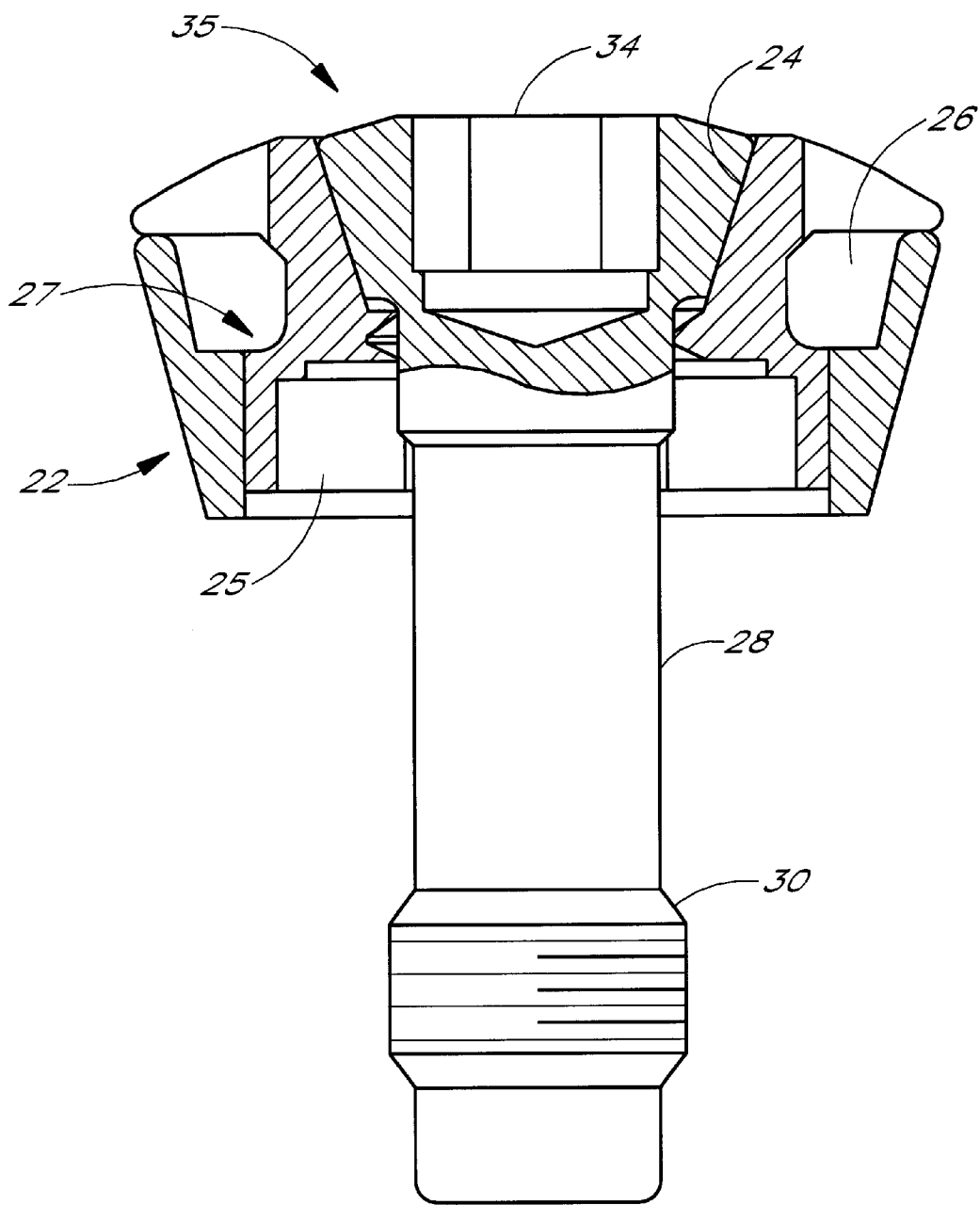
FIG. 4E is a partial cross-sectional view of a healing cap assembly as illustrated in FIG. 2.

Turning to FIGS. 4A, B, healing cap 22 is provided for covering central threaded socket 18 in implant body 12 during the healing period. Healing cap 22 has central bore 24 extending through healing cap 22 along its longitudinal axis. Preferably, healing cap 22 has a threaded region 23 within central bore 24 for engaging external threaded portion 30 on coupling screw 28. Healing cap 22 has female hexagonal recess 25 concentric with central bore 24 for receiving hexagonal projection 16. Referring to FIGS. 4C and 4D, healing cap 22 is preferably formed with a plurality of slots 26 located along the perimeter of its top surface which extend partway down into healing cap 22. The bottom of each slot is formed with an indentation 27.

When healing cap 22 is placed on top of implant body 12, female hexagonal recess receives hexagonal projection 16 such that healing cap 22 is prevented from rotating relative to implant body 12. In addition, when hexagonal projection 16 of implant body 12 mates with female recess of healing cap 22, socket 18 of implant body 12 and bore 24 of healing cap 22 are collinear. Although a hexagonally shaped protrusion and recess are used in the preferred embodiment, any shape protrusion and corresponding shaped female recess which, when in mating contact, prevents the healing cap from rotating around the male projection may be used to practice the present invention. Accordingly, those skilled in the art will readily appreciate that a wide variety of such mating protrusions and recesses may be provided, giving due consideration to the aim of providing an interlocking and/or anti-rotational interface between the cap 22 and the implant body 12 to which it is mated.

Similarly, those skilled in the art will readily appreciate that the devices depicted and described herein are not limited to the embodiment whereby the protrusion is provided on the implant body and the mating recess is provided on the healing cap. Alternatively, the protrusion or recess can be provided on either the implant body or the healing cap as desired or expedient, again giving due consideration to the aim of providing an interlocking and/or anti-rotational interface between the cap 22 and the implant body 12 to which it is mated.

Figure 5:
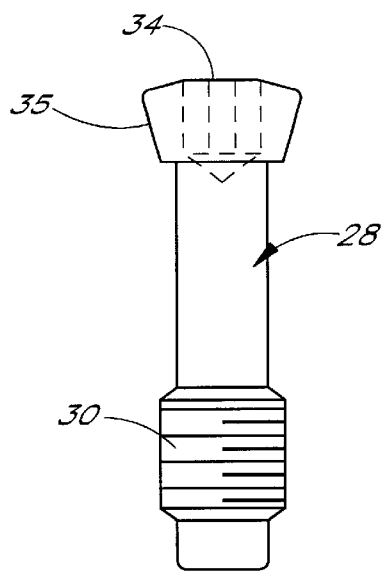
FIG. 5 is a side view of the coupling screw shown in FIG. 2.
Figure 6:
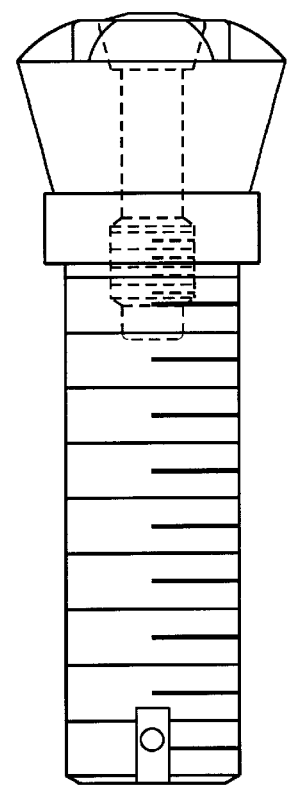
FIG. 6 is a side view of the threaded implant body, healing cap and coupling screw shown in FIG. 2.

Turning now to FIG. 5, coupling screw 28 is provided for mechanically coupling healing cap 22 to implant body 12. Coupling screw 28 extends through central bore 24 in healing cap 22 and into central socket 18 of implant body 12 (see FIG. 2). Coupling screw 28 has an externally threaded lower portion 30 which passes through threaded region 23 of central bore 24 and engages the threaded interior of central socket 18 of implant body 12. Coupling screw 28 has a hexagonal recess 34 located on the top surface. Hexagonal recess 34 allows for the insertion of a hexagonally shaped tool such as a conventional Allen® wrench to remove healing cap 22 from implant body 12 after the healing period is complete. As shown in FIG. 6, coupling screw 28 is pre-installed to mechanically couple healing cap 22 to implant body 12 before implant body 12 and healing cap 22 are inserted into the jawbone as a single unit. Preferably, the head 35 of the coupling screw 28 is tapered, as illustrated in FIG. 5, in order to allow more of the applied torque to be converted into axial load thereby more securely fastening the healing cap 22 to the implant body 12.

As shown in FIGS. 7A–D and 9, an adapter 36 provides a means for gripping healing cap 22 during the insertion of implant body 12 and healing cap 22 into an osteotomy. The top portion 41 of adapter 36 is generally annular in shape when viewed from the top along it longitudinal axis. The middle portion of adapter 36 is preferably formed with a hexagonal cross-section 40 to facilitate, if necessary, use of a torque wrench (e.g. FIGS. 19A–B) to drive adapter 36.

Adapter 36 includes a plurality of prongs 38 which are received into corresponding slots 26 formed in the top of healing cap 22 (see FIG. 4C). When prongs 38 are inserted into slots 26, adapter 36 is securely coupled to healing cap 22 and there can be no relative rotation between adapter 36 and healing cap 22. The end of each prong 38 preferably includes a lip 39 projecting radially inward for engagement with a similarly formed indentation 27 at the bottom of each slot 26 in healing cap 22 (see FIGS. 7A, 7B). The slots 26 in healing cap 22 accommodate and engage prongs 38 of adapter 36 and provide a detent function to prevent inadvertent decoupling of the adapter 36 from the healing cap 22. Lips 39 on the ends of prongs 38 are preferably tapered or rolled such that adapter 36 may be removed when desired by applying sufficient pulling force to flex prongs 38 outward thereby causing lips 39 to disengage from indentations 27 in healing cap 22.

Figure 7A:
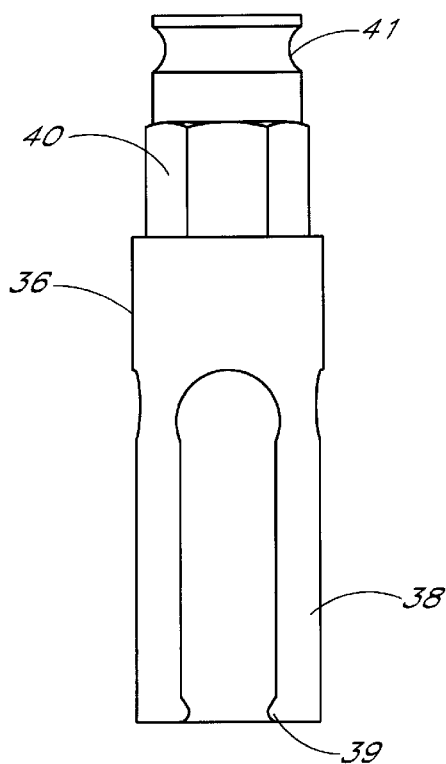
FIG. 7A is a side view of the adapter shown in FIG. 2.
Figures 7B, 7C:
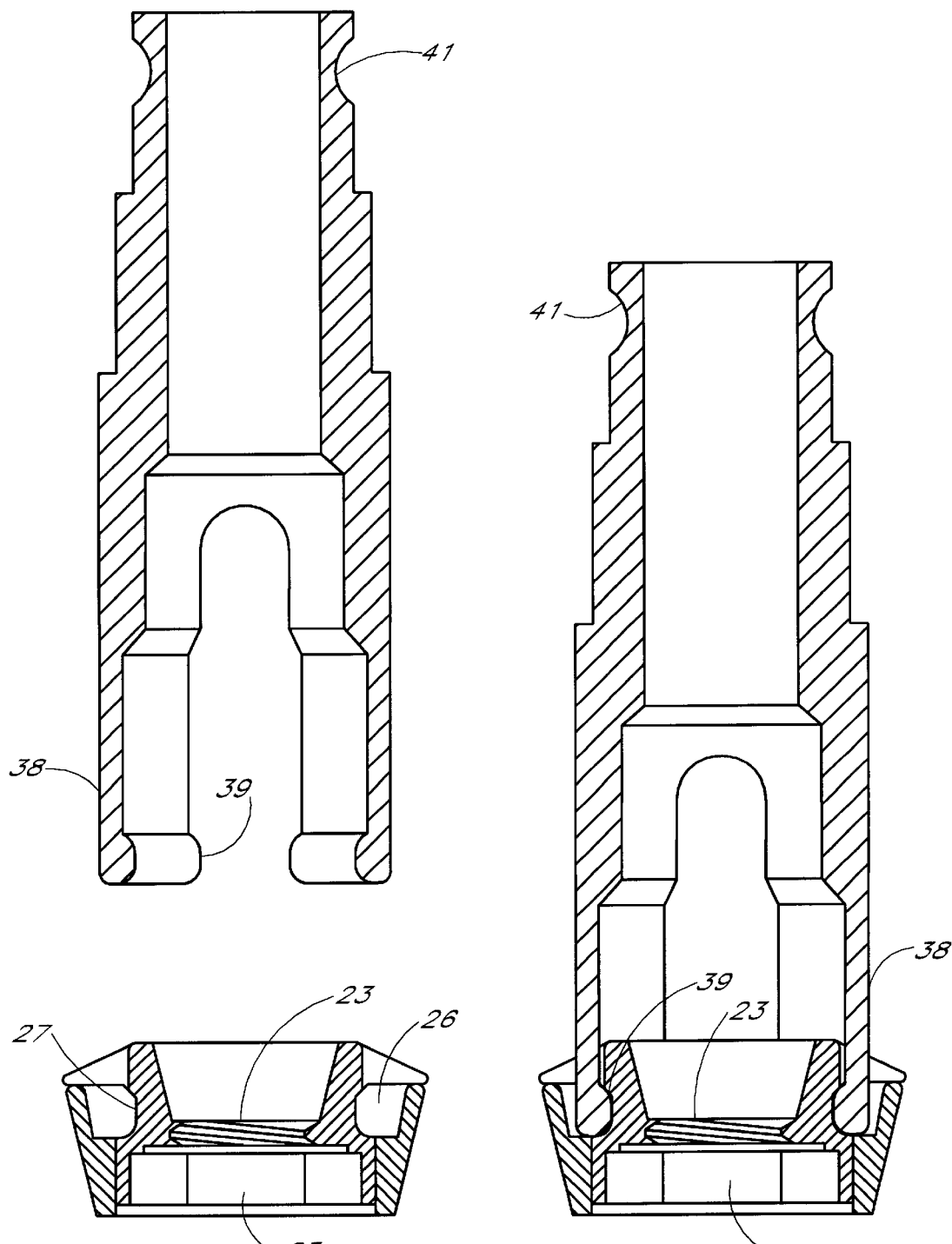
FIG. 7B is a partial cross-section view of the adapter of FIG. 7A prior to insertion into the mating top portion of a healing cap.
FIG. 7C is a partial cross-section view of the adapter of FIG. 7A after insertion into the mating top portion of a healing cap.
Figure 7D:
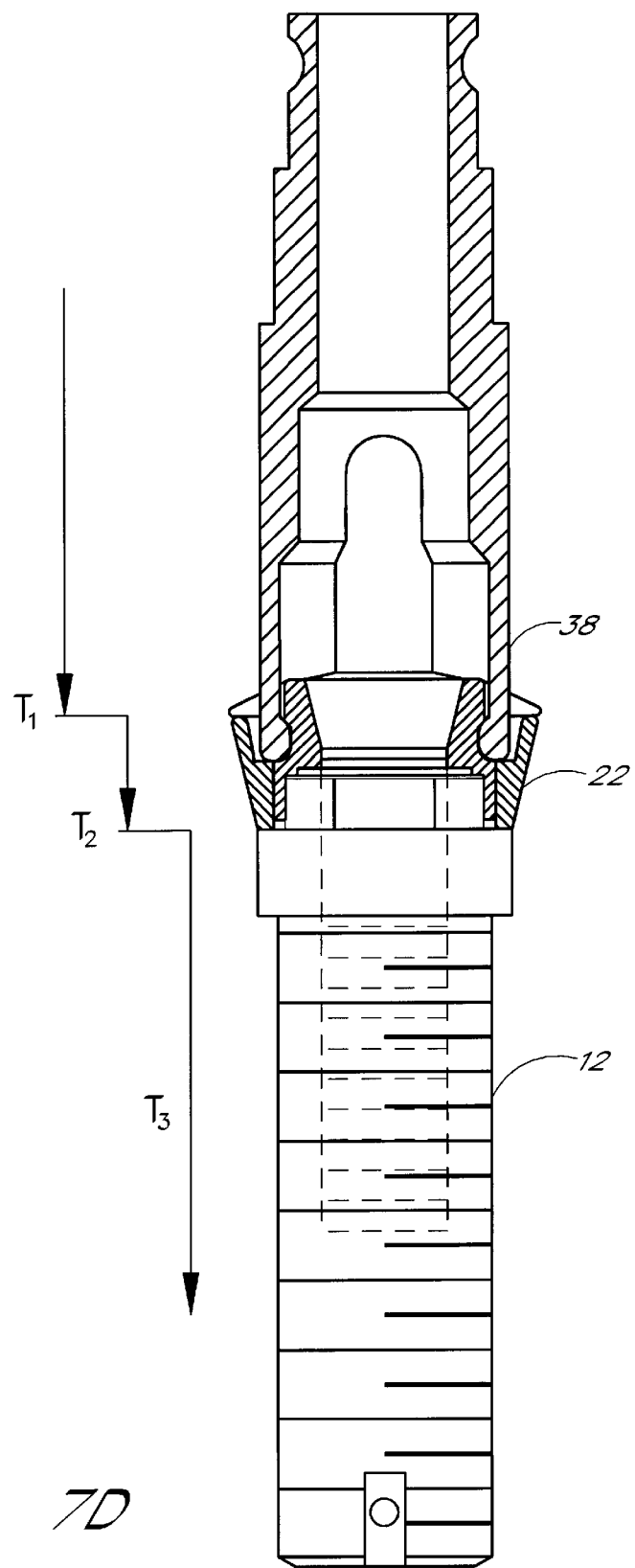
FIG. 7D is a partial cross-section view of the adapter of FIG. 7A after insertion into the mating top portion of a healing cap, illustrating the transmission of torque from the adapter to the healing cap and from the healing cap to the implant body.

FIG. 7D is a partial cross-section view of the adapter of FIG. 7A after insertion into the mating top portion of a healing cap, illustrating the transmission of torque from the adapter to the healing cap and from the healing cap to the implant body. In this manner, torque is not transmitted to the coupling screw and, therefore, over-tightening of the healing cap is avoided.

Figure 8A:
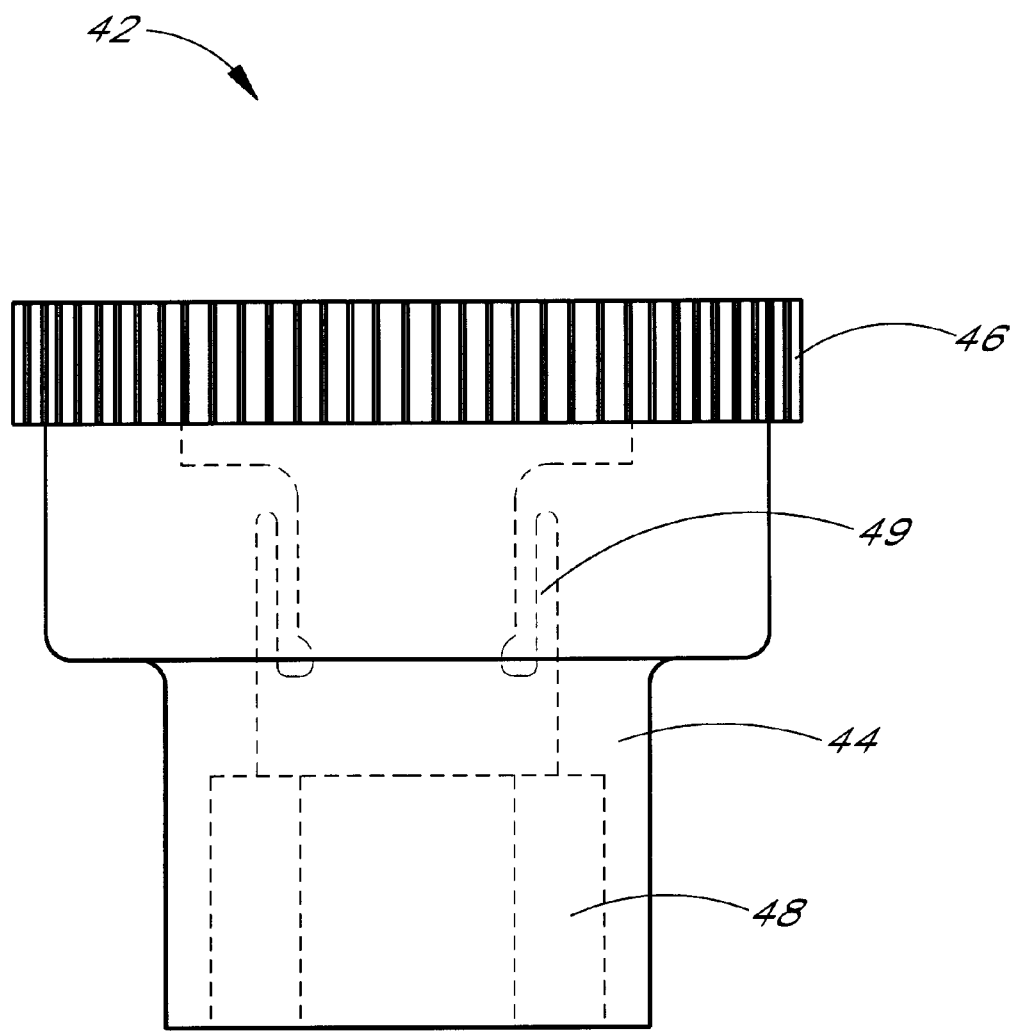
FIG. 8A is a side view of the implant carrier shown in FIG. 2.
Figure 8B:
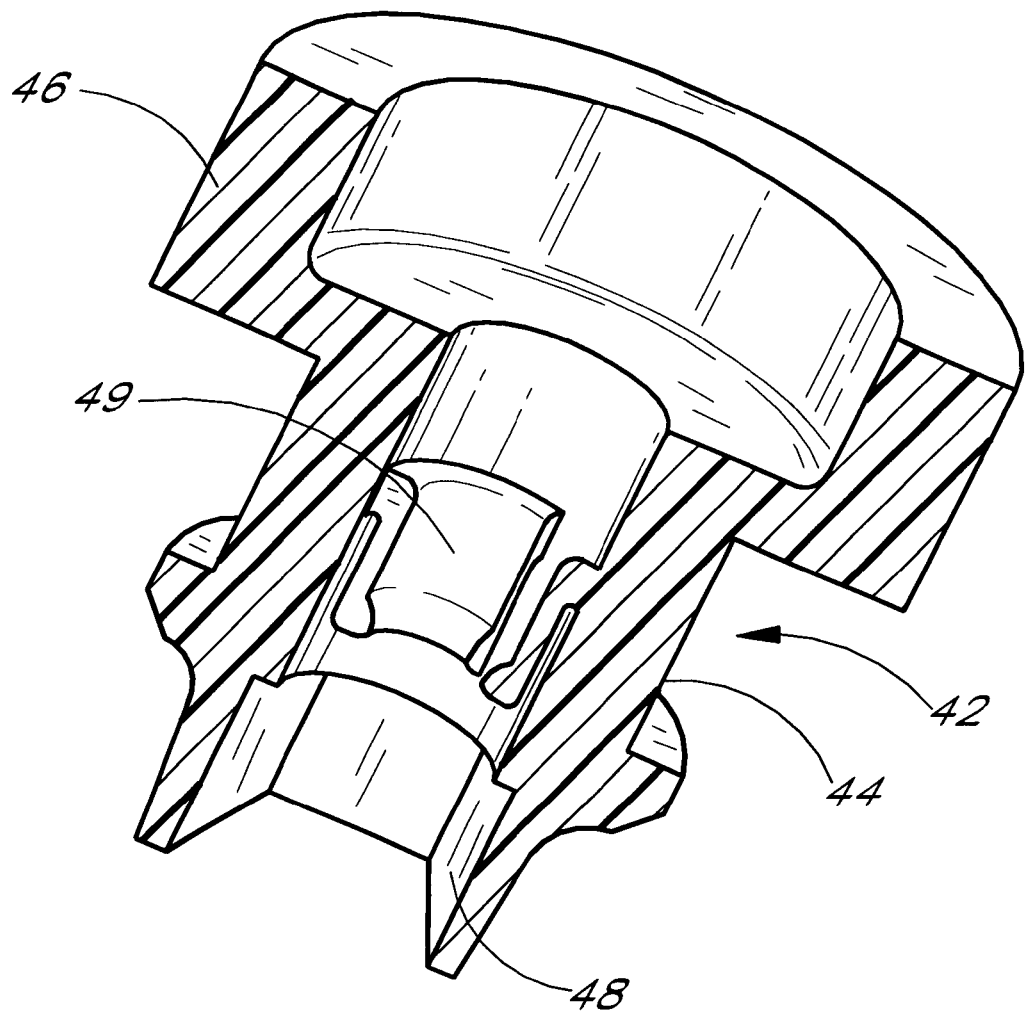
FIG. 8B is an isometric cross-sectional view of an alternative embodiment of an implant carrier as shown in FIG. 8A.

FIG. 8A illustrates an implant carrier 42 comprising a body portion 44 and flange portion 46 integrally connected to body portion 44. Body portion 44 is formed with an internal passage 48 to receive the top portion of adapter 36. Internal passage 48 is hexagonally shaped (shown in dotted lines) for receiving hexagonal cross section 40 of adapter 36 and preventing relative rotation between the two. As shown in FIG. 8B, a plurality of flexible gripping fingers 49 may be located within internal passage 48 for gripping top end 41 of adapter 36 and securely coupling implant carrier 42 to adapter 36. Preferably, the top ends of the respective fingers 49 are attached to the wall of internal passage 48 such that fingers 49 are slightly spaced away from the wall of internal passage 48. Fingers 49 extend downwards while the bottom ends of fingers 49 project radially into internal passage 48. The radial projections engage a groove in top end 41 of adapter 36. Gripping fingers 49 are formed to flex and release top end 41 of adapter 36 when sufficient longitudinal force is applied.

Figures 9, 10:
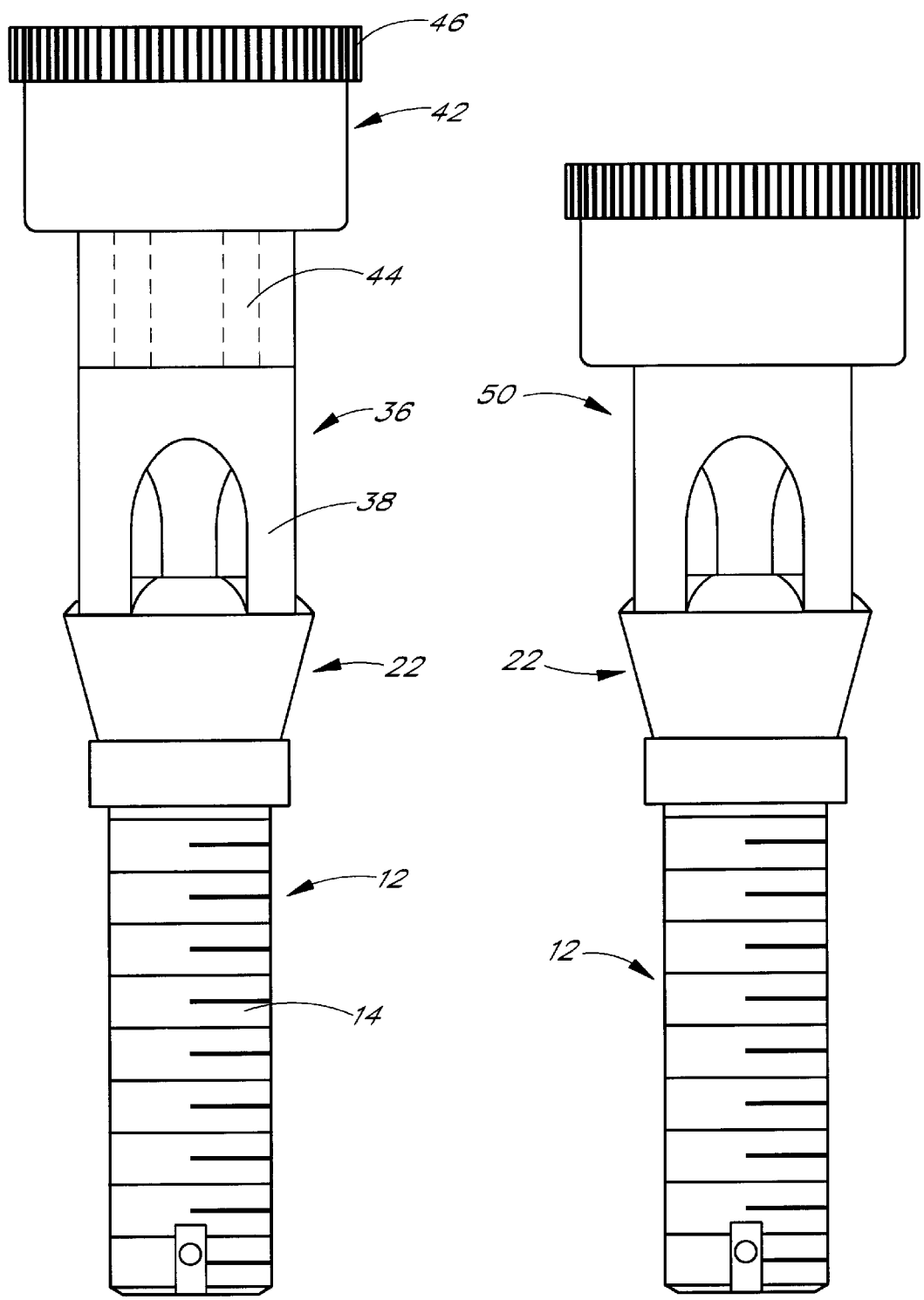
FIG. 9 is a side view of a preferred embodiment of a threaded implant assembly in accordance with the teachings of this invention.
FIG. 10 is a side view of a second embodiment of a threaded implant assembly.
Figure 11:
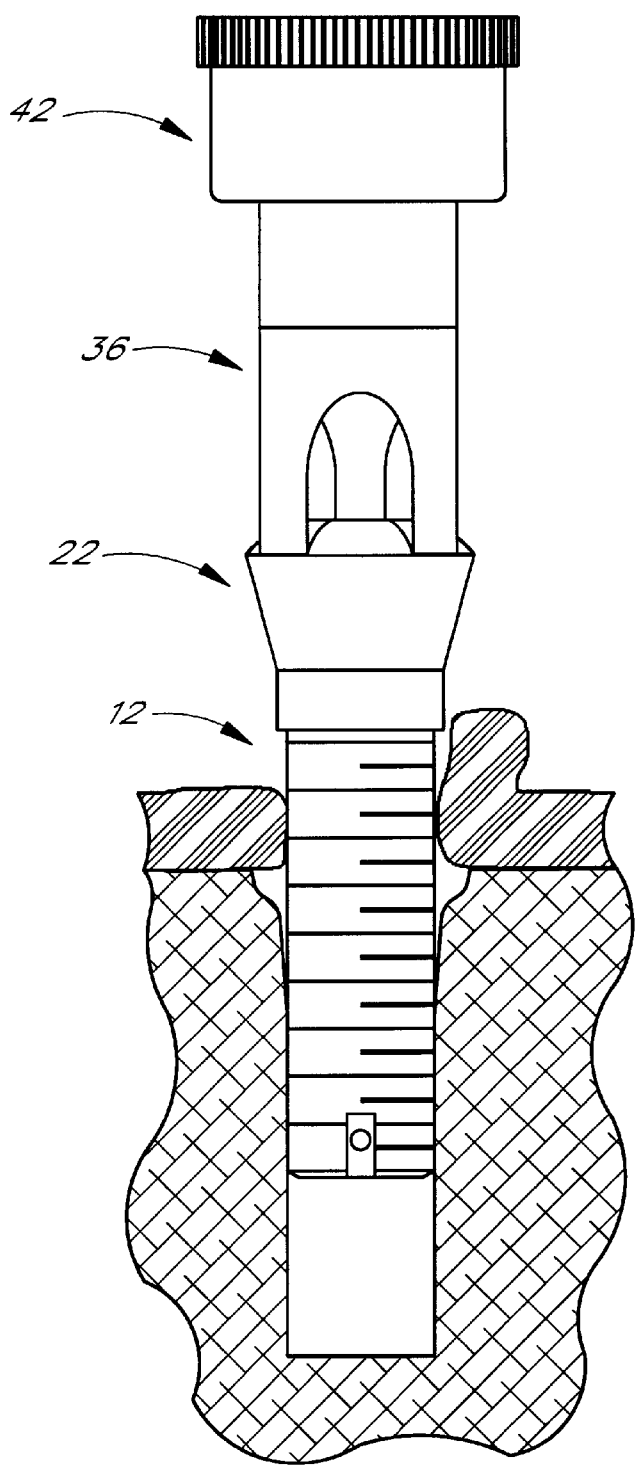
FIG. 11 illustrates the threaded implant being inserted into an osteotomy.

Flange portion 46 of implant carrier 42 is designed for easy gripping by the practitioner and has a diameter such that sufficient torque can be applied to implant body 12 by the practitioner to at least initially thread implant body 12 into an osteotomy formed in the jawbone. As shown in FIG. 9, implant carrier 42 irrationally mates with adapter 36, adapter 36 irrationally mates with healing cap 22, and healing cap 22 irrationally mates with implant body 12. Therefore, all torque applied to implant carrier 42 by the dental practitioner is transmitted directly to implant body 12.

Implant body 12, healing cap 22, coupling screw 28, and adapter 36 are all preferably made of commercially pure titanium. The implant body 12 may be coated or treated with any number of suitable surface treatments such as acid etching, hydroxylapatite coating and the like to aid in the osseointegration of implant body 12 with the jawbone. Implant carrier 42 is preferably made of a strong and durable plastic.

FIG. 10 discloses an alternative embodiment of a one-step threaded implant assembly with features and advantages in accordance with the present invention. In this embodiment, the adapter and implant carrier are integrated as a single unit 50. The integrated adapter and implant carrier 50 may be made of either commercially pure titanium or a durable plastic, as desired or expedient.

In operation, the threaded implant body and healing cap may be inserted into a jawbone in a simple one-step procedure. In accordance with the present invention, the dental implant is preferably pre-assembled and provided to the practitioner in a sterile vial or other package with healing cap 22 pre-attached to implant body 12. As noted above, healing cap 22 is mechanically coupled to implant body 12 by a coupling screw 28 which extends through central bore 24 in healing cap 22 and into central threaded socket 18 in implant body 12. Preferably, coupling screw 28 is installed by the manufacturer and is tightened to a predetermined torque setting thereby eliminating the chance of over or under tightening by the practitioner.

After a suitable osteotomy has been drilled in the patient's jawbone, the implant body 12 with the pre-attached healing cap 22 is inserted into the osteotomy. With implant carrier 42 and adapter 36 coupled to the healing cap 22/implant body 12, the practitioner inserts the implant body into the osteotomy by simultaneously pushing down and applying torque to the implant carrier 42 (see FIG. 1). Because healing cap 22 is prevented from rotating relative to implant body 12, the torque applied to healing cap 22 via the implant carrier 42 and adapter 36 is transmitted directly to implant body 12 through the mating hexes described above. If necessary, implant carrier 42 may be removed from adapter 36 and a suitable tool may be used to complete the threading of the implant into the osteotomy.

Figure 12:
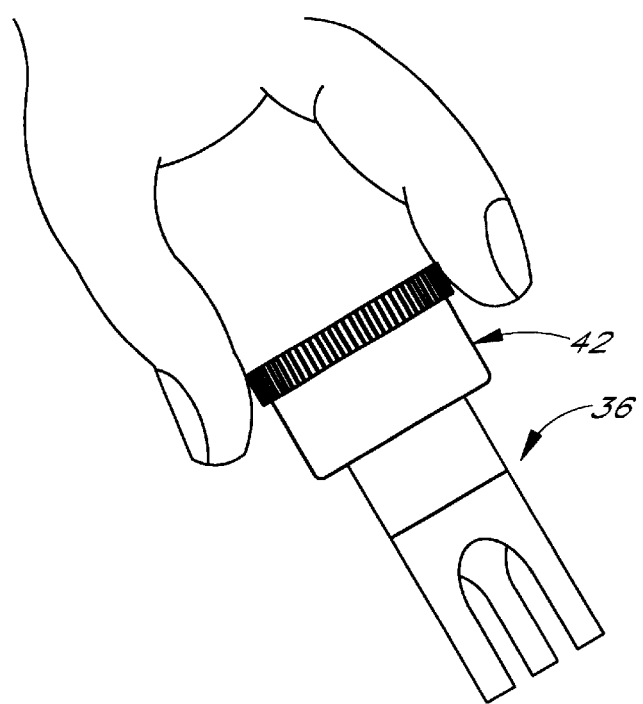
FIG. 12 illustrates the removal of the adapter and implant carrier after the threaded implant has been inserted into an osteotomy.
Figure 12:
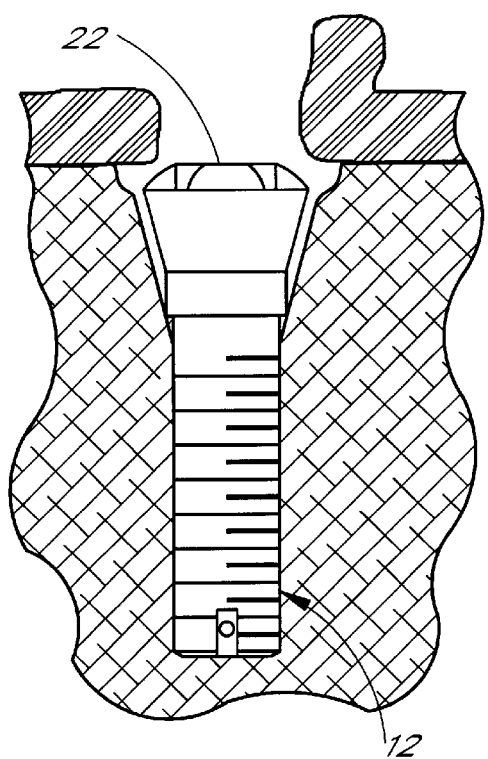

After implant body 12 and healing cap 22 are satisfactorily seated in the osteotomy, implant carrier 42 (or tool) and adapter 36 are disengaged from healing cap 22 by pulling to disengage prongs 38 from the slots 26 in healing cap 22 (see FIG. 12). Lips 39 at the end of prongs 38 on adapter 36 are tapered or rolled to allow for easy removal of adapter 36 from the healing cap 22. At this point, implant body 12, healing cap 22 and coupling screw 28 remain in the osteotomy. The gum flap is then placed over healing cap 22 and the gum tissue is sutured back together thereby covering implant body 12 and healing cap 22 and commencing the initial healing period.

After the initial healing period is complete and the implant body 12 has osseointegrated with the jawbone, an incision is made in the gum tissue to expose and then remove healing cap 22. A hexagonal tool is inserted into hexagonal recess 34 on the top of coupling screw 28 and torque is applied to the tool to remove coupling screw 28 from healing cap 22 and implant body 12. Due to the threaded region 23 in healing cap 22, coupling screw 28 remains captured within healing cap 22 after coupling screw 28 has been removed from implant body 12. This feature prevents separation of coupling screw 28 from healing cap 22 and reduces the chance of losing a component in the patient's mouth.

Coupling screw 28 has a relatively small diameter and therefore only a small amount of torque is required to break the static friction holding coupling screw 28 in implant socket 18. Also, because coupling screw was pre-installed by the manufacturer at the proper torque setting, the practitioner should be able to easily remove the coupling screw. In addition and advantageously, the top of coupling screw 28 is located in the top center of healing cap 22 where bone in growth is unlikely to reach coupling screw 28.

Figure 13:
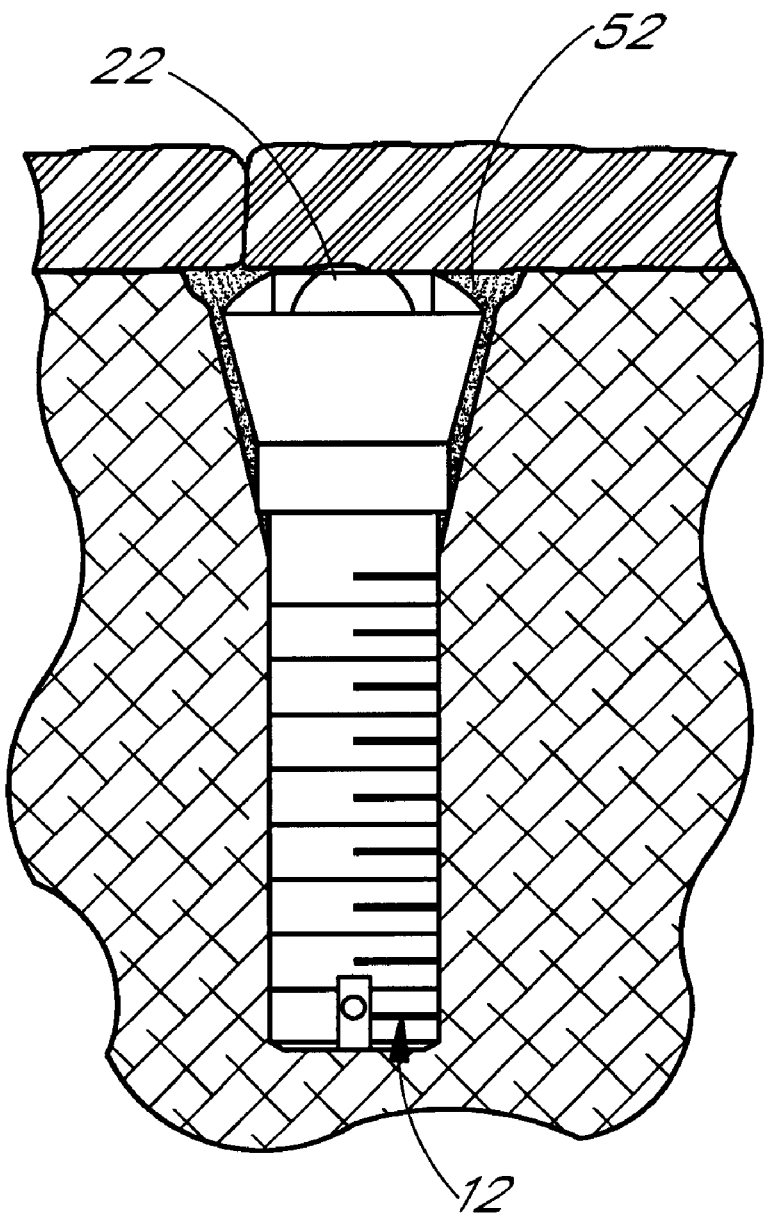
FIG. 13 illustrates the threaded implant body and healing cap of FIG. 12 osseointegrated in the jawbone following the initial healing period.

Bone in growth 52, however, can occur around the edge of the healing cap (see e.g. FIG. 13). Using a conventional healing cap that is screwed into the implant body, it may be difficult to apply sufficient shear force to break the bone in growth between the healing cap and implant body. This aspect of conventional implants is disadvantageous and can make it very difficult to safely remove the healing cap without effecting the position of the implant body and possibly damaging the osseointegration.

However, using the coupling screw of the present invention, the problem of bone in growth is largely eliminated because only coupling screw 28 needs to be unscrewed (as opposed to unscrewing the entire healing cap). Once coupling screw 28 has been removed, the practitioner can remove healing cap 22 by simply pulling it away from implant body 12. No torque is applied to healing cap 22 and therefore there is little or no chance of damaging the osseointegration between implant body 12 and the jawbone. Any bone in growth between healing cap 22 and implant body 12 can be easily removed by a bone mill and/or applying longitudinal force to pry healing cap 22 from implant body 12. Longitudinal force applied to healing cap 22 should not have any effect on the position of implant body 12; whereas torque applied to a conventional healing cap may affect the position of implant body 12 and damage the osseointegration.

Another primary advantage of the threaded dental implant of the present invention is its efficiency and ease of use. Because the implant body 12 is inserted into the osteotomy with the healing cap 22 pre-attached, the insertion process is greatly simplified. No insertion post is used in the present invention and therefore there is nothing to disassemble after the implant body is seated in the jawbone. Because there is nothing to disassemble, there is no chance of losing any small components in the patient's mouth. With the present invention, implant carrier 42 and adapter 36 are detached simply by tugging to disengage prongs 38 of adapter 36 from healing cap 22.

Because healing cap 22 is pre-attached to implant body 12, the present invention does not require screwing the healing cap into the implant body after the implant body has been inserted into the jawbone. With existing threaded implant designs, the attachment of the healing cap after the insertion of the implant body into the jawbone is often difficult to accomplish due to the surrounding tissue and blood that can obscure the implant socket from view. Also, it is difficult to ensure sterile conditions inside the implant socket and underneath the healing cap once the implant socket is exposed in the mouth. In contrast, the pre-attached healing cap of the present invention ensures sterile conditions because the implant socket is never exposed during the insertion procedure.

Another primary advantage of the present design is the increased probability of a successful and stable implantation. With conventional implants, great care must be taken not to under or over tighten the healing cap. An under tightened healing cap may lead to infection and an over tightened healing cap may be difficult to remove without damaging the osseointegration between the implant body and the jawbone. In the present invention, the healing cap is pre-attached to the implant body by the manufacturer with a coupling screw. Because the coupling screw is preset by the manufacturer, there is no chance that the coupling screw will be under or over tightened by the practitioner. This eliminates the possibility of the healing cap being too loose or too tight and therefore reduces the chances of infection or problems removing the healing cap.

Figure 14A:
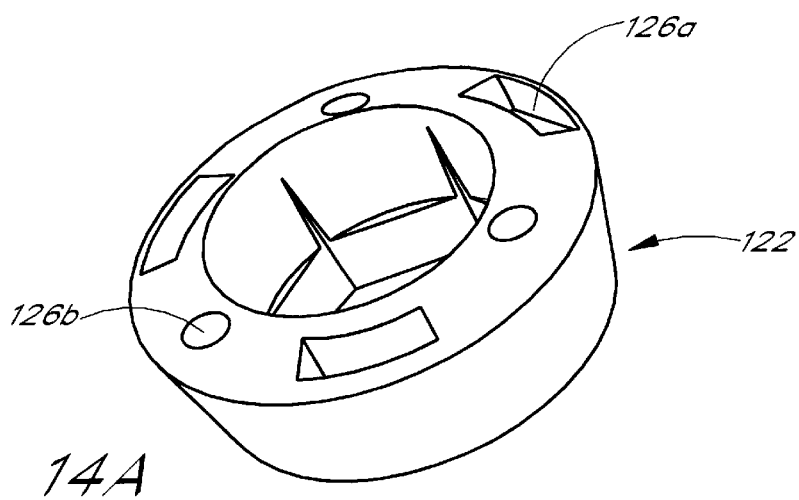
FIGS. 14A–C are perspective, top plan and side cross-sectional views, respectively, of an alternative embodiment of a healing cap having features and advantages in accordance with the present invention.
Figure 14B:
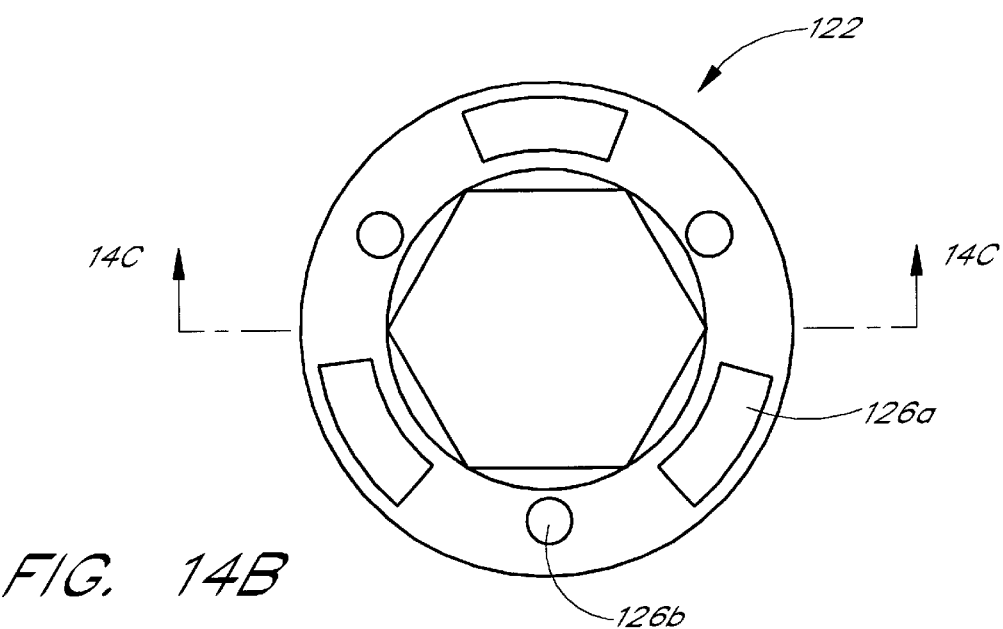
Figure 14C:
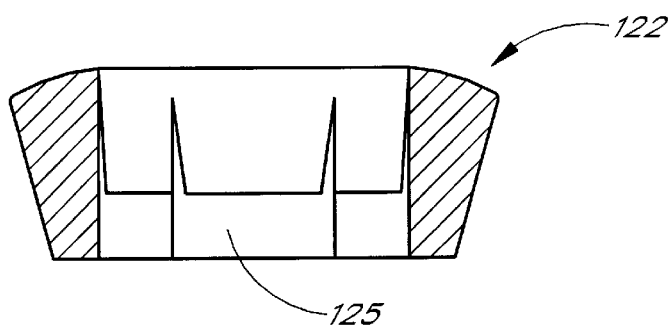

FIGS. 14A–C are perspective, top plan and side cross-sectional views, respectively, of an alternative embodiment of a healing cap 122 having features and advantages in accordance with the present invention. For purposes of clarity and brevity of disclosure, similar elements are denoted using similar reference numbers and the description of those elements will not be repeated. The healing cap 122 illustrated in FIGS. 14A–C differs from the healing cap embodiment discussed and described above in the particular size and shape of engaging recesses 126a, 126b. In this case, the recesses 126a are preferably similar to the recesses 26 described above and are undercut in a similar manner to provide for retention of corresponding prongs of an insertion tool/carrier. The recesses 126b are preferably tapered and are deeper than the recesses 126a and are adapted to receive mating metal pins 161b of an insertion tool/carrier 150 (e.g., FIG. 16B).

Figure 15A:
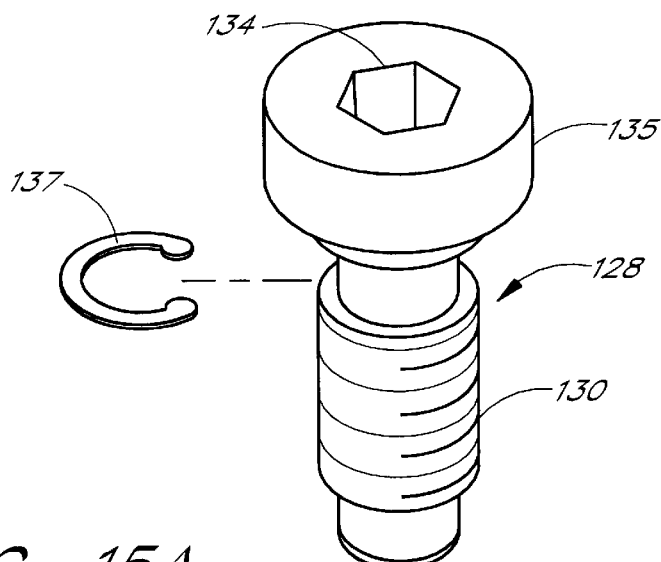
FIGS. 15A–C are perspective, top plan and side elevational views, respectively, of an alternative embodiment of a coupling screw having features and advantages in accordance with the present invention.
Figure 15B:
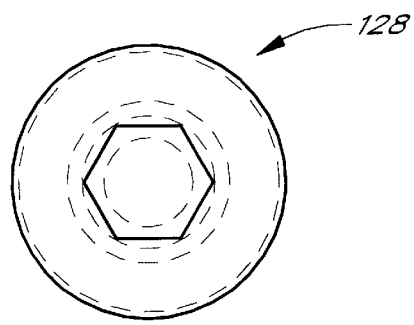
Figure 15C:
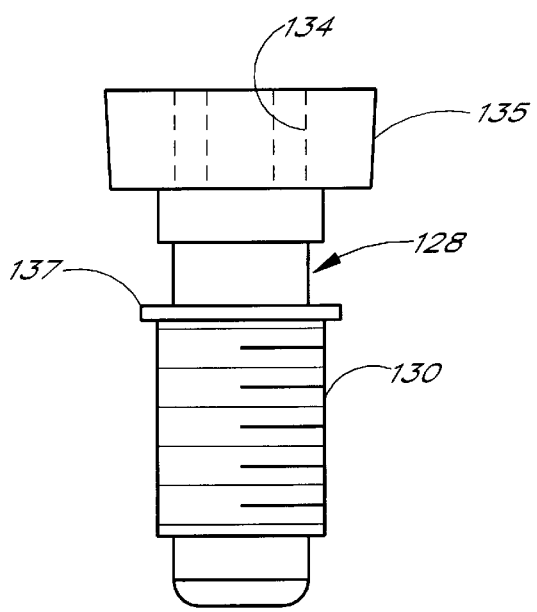

FIGS. 15A–C are perspective, top plan and side elevational views, respectively, of an alternative embodiment of a coupling screw having features and advantages in accordance with the present invention for use with the healing cap of FIG. 14. Again, for purposes of clarity and brevity of disclosure, similar elements are denoted using similar reference numbers and the description of those elements will not be repeated. The head 135 of the coupling screw 128 seats in the central bore of the healing cap 122 and is preferably tapered, as illustrated in FIG. 15C, in order to allow more of the applied torque to be converted into axial load thereby more securely fastening the healing cap 122.

Optionally, a C-shaped collar 137 or other similar component may be applied onto or formed in the shaft of the coupling screw 128 above the threads 130. This allows capturing the coupling screw 128 to the healing cap 122 once the coupling screw is inserted through the central bore of the healing cap. Alternatively, the screw shaft may be crimped or other protuberance(s) may be formed on the coupling screw shaft in order to capture the screw to the healing cap. Most preferably, the threads 130 extend up far enough on the coupling screw shaft so that when the screw is unscrewed from the implant following the initial healing period, the top of the threads 130 abut against the collar 137. This causes the collar 137 to abut against the bottom of the healing cap to lift the healing cap off of the implant. In this manner, it is easier for the practitioner to remove a healing cap that has become partially or fully covered up by calcium or bone deposits.

Figure 16A:
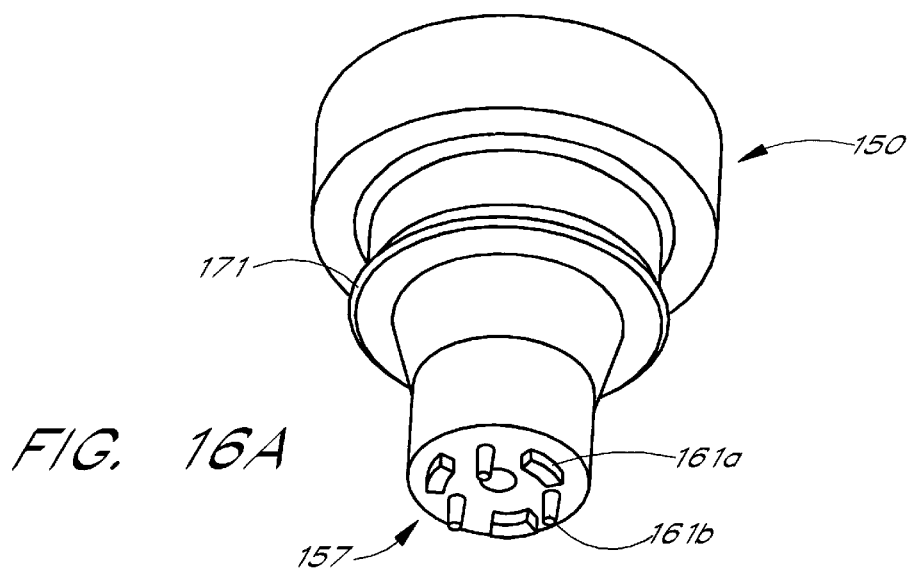
FIGS. 16A–C are perspective, side cross-sectional and top plan views, respectively, of an alternative embodiment of a carries/insertion tool having features and advantages in accordance with the present invention.
Figure 16B:
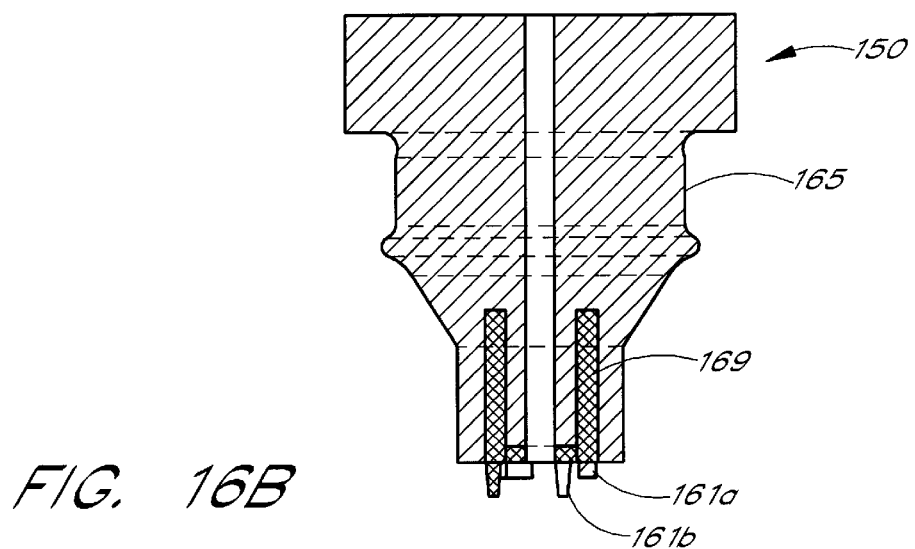
Figure 16C:
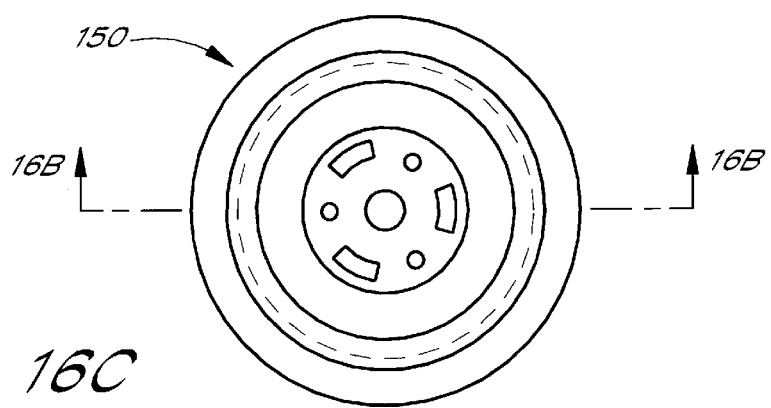

FIGS. 16A–C are perspective, side cross-sectional and top plan views, respectively, of an alternative embodiment of a carrier/insertion tool having features and advantages in accordance with the present invention. Again, for purposes of clarity and brevity of disclosure, similar elements are denoted using similar reference numbers and the description of those elements will not be repeated. The insertion tool/carrier 150 is similar in design and function to the integrated adapter and implant carrier 50 illustrated in FIG. 10. However, the insertion tool/carrier 150 illustrated in FIGS. 16A–C advantageously comprises an injection-molded thermo-plastic body 165 molded around a metal insert comprising a pin engaging tool 169. In this manner, the pins 161b are strong and are able to transmit torque from the carrier/insertion tool 150 to the healing cap and implant body. The prongs 161a are preferably similar in design and function to the prongs 38 described and illustrated above in connection with FIG. 7. The prongs 161a engage the corresponding openings and undercuts formed in the top of healing cap 122 (FIG. 14B) to retain and secure the dental implant assembly to the insertion tool/carrier during packaging and shipping and initial implant insertion. Advantageously, the insertion tool/carrier 150 is inexpensive to manufacture.

The upper portion of the insertion tool/carrier 150 has a resilient ridge 171, snaps or other flexible engaging member (s) for engaging the inner wall of a vial for packaging the dental assembly for shipment and storage. Preferably, the vial and the entire dental assembly therein is sealed or otherwise packaged to preserve the sterility of the dental assembly until the package is opened and used. Alternatively, the implant and carrier combination may be packaged separately in a sterile container or vial and the insertion too/carrier may be packaged separately (i.e. not attached to the implant assembly) in a sterile or non-sterile container, as desired or expedient.

Figure 17A:
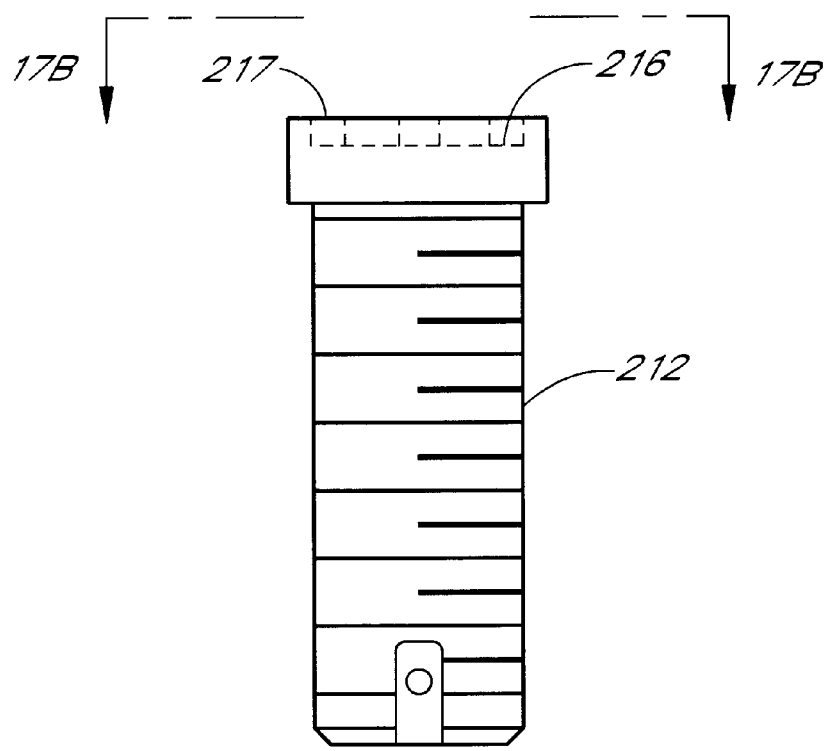
FIG. 17A is a side view of an alternative embodiment of an implant body modified from that shown in FIG. 2.
Figure 17B:
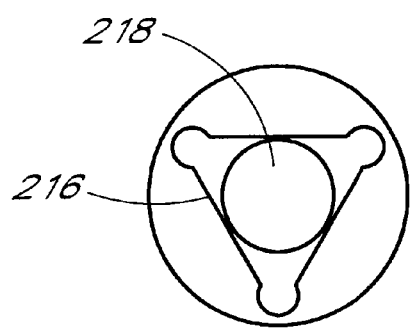
FIG. 17B is a top view of the implant body shown in FIG. 17A.
Figures 18A, 18B:
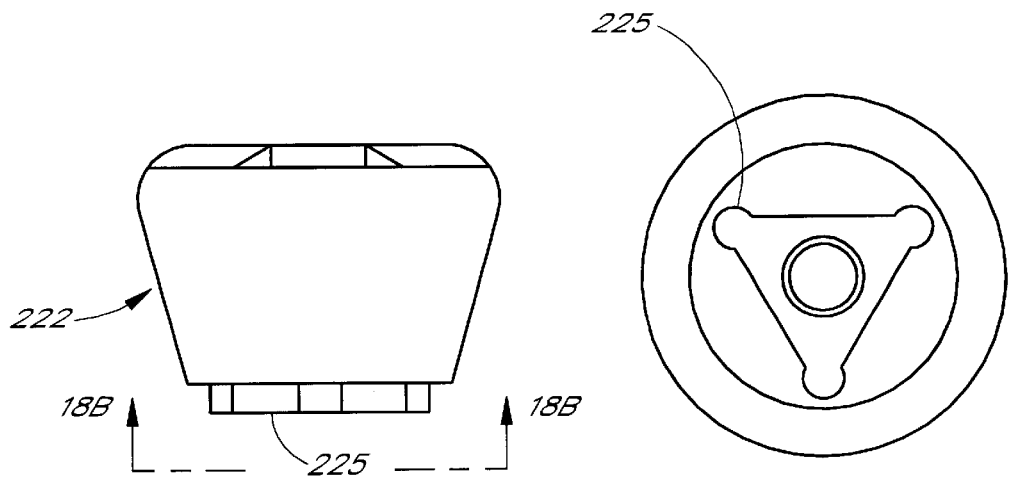
FIG. 18A is a side view of an alternative embodiment of healing cap modified from that shown in FIG. 2.
FIG. 18B is a bottom view of the healing cap shown in FIG. 18A.
Figures 18C, 18D:
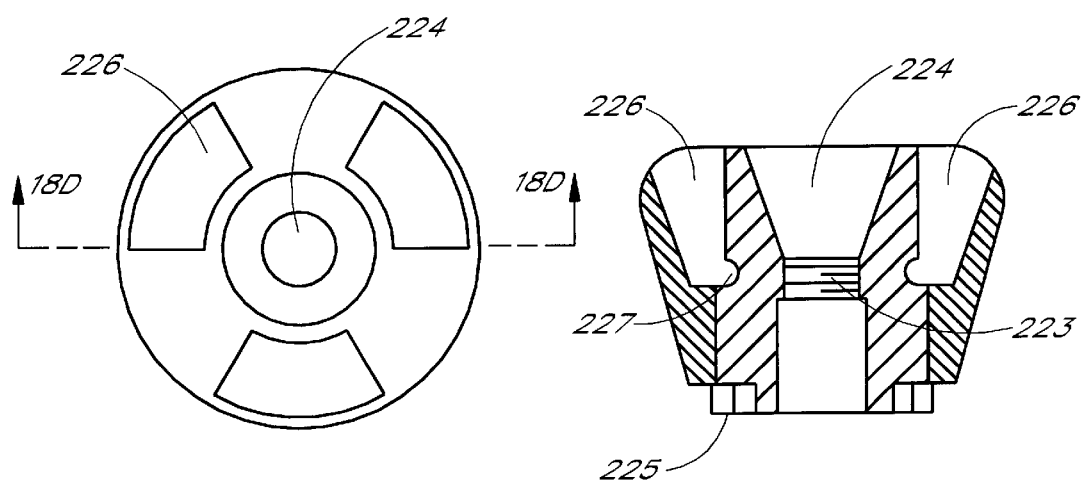
FIG. 18C is a top view of the healing cap shown in FIG. 18A.
FIG. 18D is a cross-sectional view of the healing cap shown in FIG. 18.

FIGS. 17A and 17B are side and top views, respectively, of an alternative embodiment of an implant body modified from that shown in FIGS. 3A–B. For purposes of clarity and brevity of disclosure, similar elements are denoted using similar reference numbers and the description of those elements will not be repeated. This embodiment differs from that shown and described above primarily in that a mating triangular recess 216 is provided in place of the mating hex 16 on the top of the implant body 212.

FIGS. 18A–18D are side, bottom, top and cross-section views, respectively, of an alternative embodiment of a healing cap modified from that shown in FIGS. 4A–E and adapted to mate to the implant body 212 illustrated in FIGS. 17A–B. Again, for purposes of clarity and brevity of disclosure, similar elements are denoted using similar reference numbers and the description of those elements will not be repeated. This embodiment differs from that shown and described above in connection with FIGS. 4A–E primarily in that a mating triangular protrusion 225 is provided in place of the mating hex 16 on the top of the implant body 12 to provide improved torque transmission.

Figure 19A:
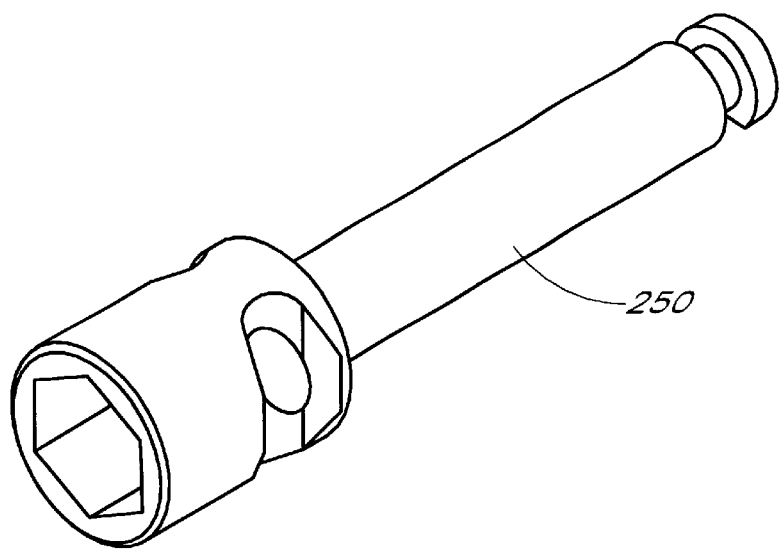
FIGS. 19A and 19B are perspective and cross-section views, respectively, of a dental handpeice driver for use in accordance with the present invention.
Figure 19B:
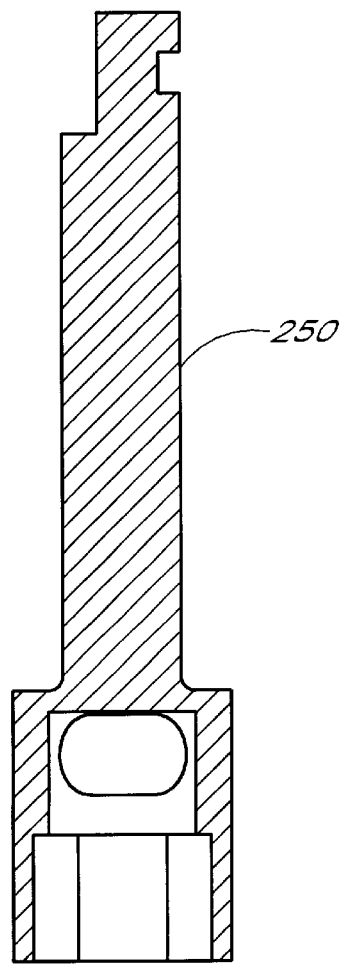
Figure 20:
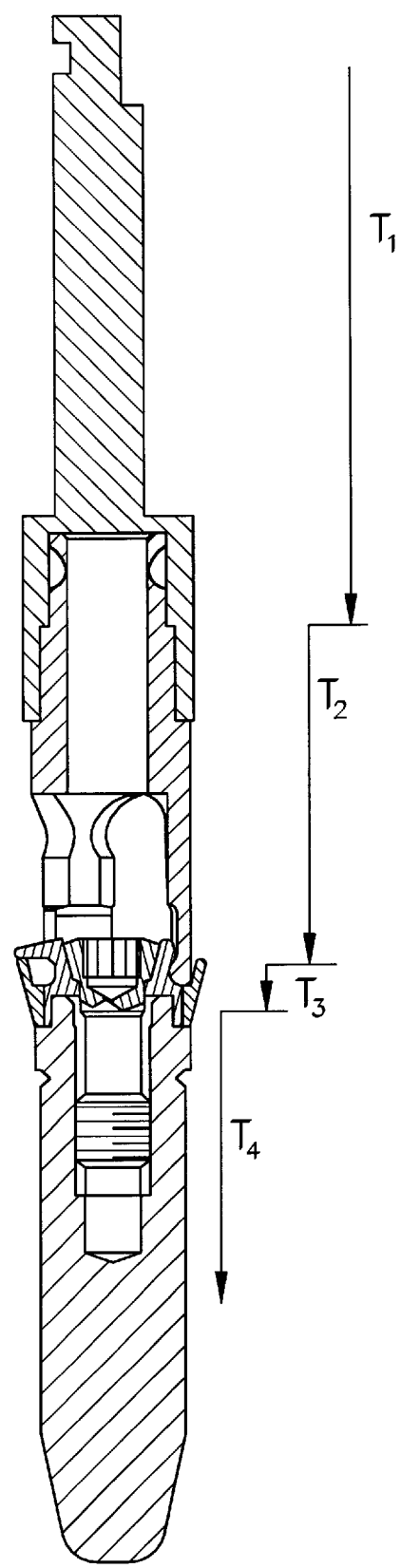
FIG. 20 is a partial cross-section view of a handpeice driver coupled to the dental implant assembly of FIG. 7D, illustrating the transmission of torque from the driver to the adapter, from the adapter to the healing cap and from the healing cap to the implant body.

FIGS. 19A and 19B are perspective and cross-section views, respectively, of a dental handpeice driver 250 for use in accordance with the present invention. FIG. 20 is a partial cross-section view of a handpeice driver coupled to the dental implant assembly of FIG. 7D, illustrating the transmission of torque T1 from the driver to the adapter, torque T2 from the adapter to the healing cap, torque T3 from the healing cap to the mating hex of the implant and torque T4 from the mating hex to the implant body. Advantageously, the torque is not transmitted to the coupling screw, thereby avoiding over-tightening of the healing cap.

The utility of the present invention will be readily apparent to those skilled in the art. The threaded implant of the present invention provides improved means for inserting a dental implant and healing screw into a patient's jawbone in an efficient one-step process. The one-step threaded implant also, desirably, provides an improved means for removing the healing screw while minimizing the possibility of disturbing the position of the implant.

Advantageously, the healing cap design of the present invention can be adapted for use in conjunction with a wide variety of dental implants. For example, attachment of the healing cap to the implant body via a small diameter coupling screw, as defined by the present invention, may be performed with or without the one-step features described above. Conventional multi-step implant designs (e.g. wherein an insertion post is used during the insertion procedure) may utilize a healing cap which is attached to the implant body by a coupling screw to protect the implant socket after the implant body is inserted. The coupling screw/healing cap design of the present invention is advantageous to virtually any implant design and may help overcome many of the problems with conventional implants which were discussed above.

While the components of the present invention have been described with a certain degree of particularity, it is manifest that many changes may be made in the specific designs, constructions and methodology herein-above described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A dental implant assembly implantable within an osteotomy formed in a jawbone comprising:

a generally cylindrical implant body having a top end and a bottom end, said implant body having external threads formed thereon for engagement with said osteotomy formed in said jawbone, said bottom end being insertable into said osteotomy so as to facilitate threaded engagement therewith, said implant body further having a threaded central socket extending from said top end toward said bottom end, said socket being open at said top end of said implant body;

a healing cap having a top and a bottom and a central bore extending therethrough, said healing cap sized and shaped so as to sealingly engage said top end of said implant body to substantially prevent bacteria or debris from entering said central socket during an initial healing period;

the top end of said implant body and/or the bottom of said healing cap further having either a protrusion or a mating recess formed therein to prevent relative rotation of said healing cap and said implant body when said healing cap is engaged with said implant body;

a coupling screw having a head seated against the top of said healing cap and a shaft extending through said central bore in said healing cap and threading into said threaded socket in said implant body, said coupling screw securely coupling said healing cap to said implant body prior to insertion into said osteotomy; and an adapter for engaging and applying torque to said top of said healing cap to cause said implant body to be threaded into said osteotomy without causing tightening of said healing cap or said coupling screw.

2. The dental implant assembly of claim 1, wherein said central bore of said healing cap has a threaded portion therein and wherein said coupling screw is threaded through said central bore past a threaded portion of said shaft whereby said healing cap and said coupling screw are loosely coupled together.

3. The dental implant assembly of claim 1, wherein a hexagonal protrusion is formed on said top end of said implant body and a hexagonal recess is formed in said bottom of said healing cap providing irrotational mating of said healing cap with said implant body.

4. The dental implant assembly of claim 1, wherein said healing cap has a plurality of slots formed along the periphery of said top of said healing cap for receiving said adapter.

5. The dental implant assembly of claim 4, wherein said adapter has a top end and a bottom end, said bottom end of said adapter being formed with a plurality of prongs insertable into said slots in said healing cap for engaging said healing cap.

6. The dental implant assembly of claim 5, wherein a middle portion of said adapter is formed with a substantially hexagonal cross section.

7. The dental implant assembly of claim 6, further comprising an implant carrier with a hexagonally shaped internal passage for receiving said hexagonal cross section of said middle portion of said adapter.

8. A dental implant assembly comprising:

an implant body having a top end and a bottom end, said implant body having a threaded central socket formed therein extending through said top end;

a healing cap having a top and a bottom and a central though-bore, said healing cap sized and shaped so as to engage said top end of said implant body and substantially prevent bacteria or debris from entering said central socket during an initial healing period;

the top end of said implant body and/or the bottom of said healing cap further having either a protrusion or a mating recess formed therein to prevent relative rotation of said healing cap and said implant body when said healing cap is engaged with said implant body;

a coupling screw having a shaft extending through said central though-bore in said healing cap and threading into said central socket in said implant body, said coupling screw securely attaching said healing cap to said implant body prior to insertion in an osteotomy formed in a jaw bone;

wherein said implant body, said healing cap and said coupling screw are all pre-assembled and packaged in a sterile package.

9. The dental implant assembly of claim 8, wherein said central through-bore of said healing cap has a threaded portion therein and wherein said coupling screw is threaded through said central bore past a threaded portion of said shaft whereby said healing cap and said coupling screw are loosely coupled together.

10. The dental implant assembly of claim 8, wherein a hexagonal protrusion is formed on said top end of said implant body and a hexagonal recess is formed in said bottom of said healing cap providing irrotational mating of said healing cap with said implant body.

11. The dental implant assembly of claim 8, wherein said healing cap further comprises a plurality of slots formed along the periphery of said top of said healing cap for receiving a torque driver adapter.

12. The dental implant assembly of claim 11, further comprising a torque driver adapter having a top end and a bottom end, said bottom end of said adapter being formed with a plurality of prongs insertable into said slots in said healing cap for engaging and applying torque to said healing cap to thread said implant body into said hole formed in said jaw bone.

13. The dental implant assembly of claim 12, wherein a middle portion of said adapter is formed with a substantially hexagonal cross section.

14. The dental implant assembly of claim 13, further comprising an implant carrier with a hexagonally shaped internal passage for receiving said hexagonal cross section of said middle portion of said adapter.

15. A healing cap assembly for sealing the top of an implant body of the type having a threaded central socket opening through the top of said implant body during an initial healing period, said healing cap assembly comprising:

a cap portion having a central bore extending in an axial direction, said cap portion sized and shaped so as to sealingly engage said top end of said implant body to substantially prevent bacteria or debris from entering said central socket during an initial healing period;

a coupling screw insertable through said central bore in said cap portion and threading into said threaded central socket of said implant body for securely attaching said cap portion to said implant body; and said cap portion having an axial length which is dimensioned such that adjacent gingival tissue can be sutured over said cap portion to cover said cap portion during said initial healing period.

16. The healing cap assembly of claim 15, wherein said central bore of said cap portion has a threaded portion therein and wherein said coupling screw is threaded through said central bore past said threaded portion thereof whereby said cap portion and said coupling screw are loosely coupled together.

17. The healing cap assembly of claim 15, wherein a hexagonal recess is formed in a bottom portion of said cap portion for matingly and irrationally engaging a corresponding protrusion formed on said top of said implant body for providing irrotational mating of said cap portion with said implant body.

18. The healing cap assembly of claim 15, wherein said cap portion further comprises a plurality of slots formed along the periphery of a top portion of said healing cap for receiving a torque driver adapter.

19. The healing cap assembly of claim 18 in combination with a torque driver adapter having a top end and a bottom end, said bottom end of said adapter being formed with a plurality of prongs insertable into said slots in said cap portion for engaging and applying torque to said cap portion to thread said implant body into said hole formed in said jaw bone without over-tightening of said healing cap assembly.

20. The combination of claim 19, wherein a middle portion of said adapter is formed with a substantially hexagonal cross section.

21. The combination of claim 20, further comprising an implant carrier with a hexagonally shaped internal passage for receiving said hexagonal cross section of said middle portion of said adapter.

22. The healing cap assembly of claim 15 secured to a threaded implant body prior to insertion in an osteotomy formed in a jawbone.

23. A method of inserting a threaded dental implant comprising:

drilling a hole in the jawbone below the gums;

transporting a threaded implant body and a pre-attached healing cap to said hole in said jawbone while said healing cap is secured to said implant body by a coupling screw;

applying torque to said implant body via a tool engaging the top of said healing cap to thread said implant body into said hole in said jaw bone; and disengaging said tool from said healing cap after said implant is properly seated in said hole in said jawbone.

24. The method of claim 23, comprising the further step of threading said hole formed in said jaw bone so as to threadingly receive said threaded implant body.

25. The method of claim 23, comprising the further step of suturing the gums over said seated implant body and said pre-attached healing cap during an initial healing period without removing said healing cap or exposing the surface of said implant beneath said healing cap.

26. A dental implant kit for implanting a dental implant within an osteotomy formed in a jawbone comprising:

a generally cylindrical implant body having a top end and a bottom end, said implant body having external threads formed thereon for engagement with said osteotomy formed in said jawbone, said bottom end being insertable into said osteotomy so as to facilitate threaded engagement therewith, said implant body further having a threaded central socket extending from said top end toward said bottom end, said socket being open at said top end of said implant body;

a healing cap having a top and a bottom and a central bore extending therethrough, said healing cap sized and shaped so as to sealingly engage said top end of said implant body to substantially prevent bacteria or debris from entering said central socket during an initial healing period;

the top end of said implant body and/or the bottom of said healing cap further having either a protrusion or a mating recess formed therein to prevent relative rotation of said healing cap and said implant body when said healing cap is engaged with said implant body; and a coupling screw having head seated against the top of said healing cap and a shaft extending through said central bore in said healing cap and threading into said threaded socket in said implant body, said coupling screw securely coupling said healing cap to said implant body;

wherein said implant body, said healing cap and said coupling screw are all pre-assembled and packaged in a sterile vial or other container.

27. A dental implant assembly comprising:

an implant body having a top end and a bottom end, said implant body having a threaded central socket formed therein extending through said top end;

a healing cap having a top and a bottom and a central though-bore, said healing cap sized and shaped so as to engage said top end of said implant body and substantially prevent bacteria or debris from entering said central socket during an initial healing period;

the top end of said implant body and/or the bottom of said healing cap further having either a protrusion or a mating recess formed therein to prevent relative rotation of said healing cap and said implant body when said healing cap is engaged with said implant body;

a coupling screw having a shaft extending through said central though-bore in said healing cap and threading into said central socket in said implant body, said coupling screw securely attaching said healing cap to said implant body prior to insertion in an osteotomy formed in a jaw bone;

said healing cap further having a plurality of slots formed along the periphery of said top of said healing cap; and a torque driver adapter having a top end and a bottom end, said bottom end of said adapter being formed with a plurality of prongs insertable into said slots in said healing cap for engaging and applying torque to said healing cap to thread said implant body into said hole formed in said jaw bone.

28. The dental implant assembly of claim 27, wherein said central through-bore of said healing cap has a threaded portion therein and wherein said coupling screw is threaded through said central bore past a threaded portion of said shaft whereby said healing cap and said coupling screw are loosely coupled together.

29. The dental implant assembly of claim 27, wherein a hexagonal protrusion is formed on said top end of said implant body and a hexagonal recess is formed in said bottom of said healing cap providing irrotational mating of said healing cap with said implant body.

30. The dental implant assembly of claim 27, wherein a middle portion of said adapter is formed with a substantially hexagonal cross section.

31. The dental implant assembly of claim 30, further comprising an implant carrier with a hexagonally shaped internal passage for receiving said hexagonal cross section of said middle portion of said adapter.

32. The dental implant assembly of claim 27, wherein said top end of said adapter is formed with a substantially annular groove.

33. The dental implant assembly of claim 32, further comprising an implant carrier having a plurality of gripping fingers for engaging said groove of said adapter to releasably hold said adapter.

34. A healing cap assembly for sealing the top of an implant body of the type having a threaded central socket opening through the top of said implant body during an initial healing period, said healing cap assembly comprising:

- a cap portion having a central bore and a top portion, said cap portion sized and shaped so as to sealingly engage said top of said implant body to substantially prevent bacteria or debris from entering said central socket during an initial healing period;
- a coupling screw insertable through said central bore in said cap portion and threading into said threaded central socket of said implant body for securely attaching said cap portion to said implant body;
- said cap portion further having a plurality of slots formed along the periphery of said top portion of said cap portion; and
- a torque driver adapter having a top end and a bottom end, said bottom end of said adapter being formed with a plurality of prongs insertable into said slots in said cap portion for engaging and applying torque to said cap portion to thread said implant body into said hole formed in said jaw bone without over-tightening of said healing cap assembly.

35. The healing cap assembly of claim 34, wherein said central bore of said cap portion has a threaded portion therein and wherein said coupling screw is threaded through said central bore past said threaded portion thereof whereby said cap portion and said coupling screw are loosely coupled together.

36. The healing cap assembly of claim 34, wherein a hexagonal recess is formed in a bottom portion of said cap portion for matingly and irrationally engaging a corresponding protrusion formed on said top of said implant body for providing irrotational mating of said cap portion with said implant body.

37. The healing cap assembly of claim 34, wherein a middle portion of said adapter is formed with a substantially hexagonal cross section.

38. The healing cap assembly of claim 37, further comprising an implant carrier with a hexagonally shaped internal passage for receiving said hexagonal cross section of said middle portion of said adapter.

39. The healing cap assembly of claim 34 secured to a threaded implant body prior to insertion in an osteotomy formed in a jawbone.

40. A method of inserting a dental implant into an osteotomy formed in a jawbone, comprising the steps of:

- providing an implant having a top end and a bottom end and a threaded central socket extending through said top end;
- providing a healing cap having a top and a bottom and a central through-bore;
- providing a coupling screw having a shaft extending through said central through-bore in said healing cap and threading into said central socket in said implant to secure said healing cap to said implant; and
- simultaneously installing said implant, said healing cap and said coupling screw as a unit in said osteotomy.

41. The method of claim 40, comprising the further step of providing a torque driver adapter engaged with said top of said healing cap to thread said implant into said osteotomy.

42. The method of claim 41, comprising the further step of providing an implant carrier engaged with said torque driver adapter.

43. The method of claim 40, comprising the further step of applying torque to said top of said healing cap to cause said implant to be installed into said osteotomy.

44. The method of claim 40, wherein said central through-bore of said healing cap has a threaded portion therein and wherein said coupling screw is threaded through said central bore past a threaded portion of said shaft whereby said healing cap and said coupling screw are loosely coupled together.

45. The method of claim 40, wherein a hexagonal protrusion is formed on said top end of said implant body and a hexagonal recess is formed in said bottom of said healing cap providing irrotational mating of said healing cap with said implant.

46. The method of claim 40, wherein said healing cap has plurality of slots formed along the periphery of said top of said healing cap for receiving a torque driver adapter.

* * * * *

UNITED STATES PATENT AND TRADEMARK OFFICE
CERTIFICATE OF CORRECTION

PATENT NO. : 6,312,260 B1  
DATED : November 6, 2001  
INVENTOR(S) : Kumar et al.

It is certified that error appears in the above-identified patent and that said Letters Patent is hereby corrected as shown below:

Column 17,  
Line 7, "irrationally" should read -- irrotationally --.

Column 19,  
Line 35, "irrationally" should read -- irrotationally --.

Signed and Sealed this

Twenty-third Day of July, 2002

Attest:

JAMES E. ROGAN  
Attesting Officer        Director of the United States Patent and Trademark Office